United States Patent
Woolf et al.

(10) Patent No.: US 10,365,267 B2
(45) Date of Patent: Jul. 30, 2019

(54) METHODS AND ASSAYS RELATING TO SEPIAPTERIN REDUCTASE INHIBITION

(71) Applicant: CHILDREN'S MEDICAL CENTER CORPORATION, Boston, MA (US)

(72) Inventors: Clifford J. Woolf, Newton, MA (US); Alexandra S. Latini, Brookline, MA (US); Nick A. Andrews, Cambridge, MA (US); Alban Latremoliere, Boston, MA (US); Michael Costigan, Cambridge, MA (US)

(73) Assignee: CHILDREN'S MEDICAL CENTER CORPORATION, Boston, MA (US)

( * ) Notice: Subject to any disclaimer, the term of this patent is extended or adjusted under 35 U.S.C. 154(b) by 0 days.

(21) Appl. No.: 15/516,956

(22) PCT Filed: Oct. 29, 2015

(86) PCT No.: PCT/US2015/057963
§ 371 (c)(1),
(2) Date: Apr. 5, 2017

(87) PCT Pub. No.: WO2016/069847
PCT Pub. Date: May 6, 2016

(65) Prior Publication Data
US 2017/0307591 A1    Oct. 26, 2017

Related U.S. Application Data

(60) Provisional application No. 62/073,320, filed on Oct. 31, 2014.

(51) Int. Cl.
*A61K 31/4045* (2006.01)
*G01N 33/50* (2006.01)
(Continued)

(52) U.S. Cl.
CPC ..... *G01N 33/5038* (2013.01); *A61K 31/4045* (2013.01); *A61K 31/519* (2013.01);
(Continued)

(58) Field of Classification Search
CPC .................................................... A61K 31/519
See application file for complete search history.

(56) References Cited

U.S. PATENT DOCUMENTS 5,877,176 A * 3/1999 Gross .................. A61K 31/165
514/251
7,906,520 B2    3/2011 Woolf et al.
(Continued)

FOREIGN PATENT DOCUMENTS

WO    2005/048926 A2    6/2005

OTHER PUBLICATIONS

Sawabe et al., Molecular Genetics and Metabolism, 2008;94:410-416.*

(Continued)

*Primary Examiner* — San Ming R Hui
(74) *Attorney, Agent, or Firm* — Nixon Peabody LLP; David S. Resnick; Nicole D. Kling

(57) ABSTRACT

Described herein are methods and assays relating to the inhibition of sepiapterin reductase and measuring said inhibition by measuring the level of sepiapterin. In some embodiments, the methods can further relate to treating a subject with BH4 and/or BH2.

9 Claims, 13 Drawing Sheets

Specification includes a Sequence Listing.

(51) Int. Cl.
*C12Q 1/26* (2006.01)
*A61K 31/519* (2006.01)
*G01N 33/487* (2006.01)

(52) U.S. Cl.
CPC ............. *C12Q 1/26* (2013.01); *G01N 33/487* (2013.01); *G01N 33/5008* (2013.01); *G01N 2560/00* (2013.01); *G01N 2800/52* (2013.01)

(56) References Cited

U.S. PATENT DOCUMENTS

| | | | |
|---|---|---|---|
| 8,669,258 B2 | 3/2014 | Pasricha et al. | |
| 2012/0322800 A1* | 12/2012 | Blagg | C07D 209/14 514/235.2 |
| 2013/0197000 A1 | 8/2013 | Hasegawa et al. | |
| 2013/0210826 A1 | 8/2013 | Woolf et al. | |
| 2014/0056998 A1 | 2/2014 | Clelland et al. | |

OTHER PUBLICATIONS

Bracher et al., "Biosynthesis of pteridines NMR studies on the reaction mechanisms of GTP cyclohydrolase I, pyruvoyltetrahydropterin synthase, and sepiapterin reductase." Journal of Biological Chemistry 273(43):28132-28141 (1998).
Chidley et al., "A yeast-based screen reveals that sulfasalazine inhibits tetrahydrobiopterin biosynthesis." Nature Chemical Biology 7(6):375-383 (2011).
D'Sa et al., "Tetrahydrobiopterin biosynthesis in C6 glioma cells: induction of GTP cyclohydrolase I gene expression by lipopolysaccharide and cytokine treatment" Molecular brain research 41(1-2):105-110 (1996).
Franscini et al., "Critical role of interleukin-1β for transcriptional regulation of endothelial 6-pyruvoyltetrahydropterin synthase." Arteriosclerosis, Thrombosis, and Vascular Biology 23(11):e50-e53 (2003).
Haruki et al., "Tetrahydrobiopterin biosynthesis as an off-target of sulfa drugs." Science 340(6135):987-991 (2013).
Hirakawa et al., "Expression analysis of the aldo-keto reductases involved in the novel biosynthetic pathway of tetrahydrobiopterin in human and mouse tissues." Journal of Biochemistry 146(1):51-60 (2009).
Ishii et al., "Reduction of GTP cyclohydrolase I feedback regulating protein expression by hydrogen peroxide in vascular endothelial cells." Journal of Pharmacological Sciences 97(2):299-302 (2005).
Levine et al., "Immunological evidence for the requirement of sepiapterin reductase for tetrahydrobiopterin biosynthesis in brain." Journal of Neurochemistry 54(4):1218-1224 (1990).
Nakanishi et al., "6-Acetonylisoxanthopterin: A Potent Inhibitor of Sepiapterin Reductase." Pteridines 3(3):165-166 (1991).
Nichol et al., "Biosynthesis and metabolism of tetrahydrobiopterin and molybdopterin." Annual Review of Biochemistry 54(1):729-764 (1985).
Sawabe et al., "Cellular uptake of sepiapterin and push-pull accumulation of tetrahydrobiopterin." Molecular Genetics and Metabolism 94(4):410-416 (2008).
Smith et al., "New inhibitors of sepiapterin reductase. Lack of an effect of intracellular tetrahydrobiopterin depletion upon in vitro proliferation of two human cell lines." Journal of Biological Chemistry 267(8):5599-5607 (1992).
Sueoka et al., "Purification and characterization of sepiapterin reductase from rat erythrocytes." Biochimica et Biophysica Acta (BBA)—General Subjects 717(2):265-271 (1982).
Thöny et al., "Tetrahydrobiopterin biosynthesis, regeneration and functions." Biochemical Journal 347(1):1-16 (2000).
Werner et al., "Tetrahydrobiopterin biosynthetic activities in human macrophages, fibroblasts, THP-1, and T 24 cells. GTP-cyclohydrolase I is stimulated by interferon-gamma, and 6-pyruvoyl tetrahydropterin synthase and sepiapterin reductase are constitutively present." Journal of Biological Chemistry 265(6):3189-3192 (1990).
Werner et al., "Tetrahydrobiopterin: biochemistry and pathophysiology." Biochemical Journal 438(3):397-414 (2011).
Werner-Felmayer et al., "Induction of GTP cyclohydrolase I by bacterial lipopolysaccharide in the rat." FEBS Letters 322(3):223-226 (1993).
Zorzi et al., "Detection of sepiapterin in CSF of patients with sepiapterin reductase deficiency." Molecular Genetics and Metabolism 75(2):174-177 (2002).
Hasegawa et al. "Delivery of exogenous tetrhydrobiopterin (BH4) to cells of target organs: Role of salvage pathway and uptake of its precursor in effective elevatin of tissue BH4." Molecule Genetics and Metabolism 86(1):2-10 (2005).

* cited by examiner

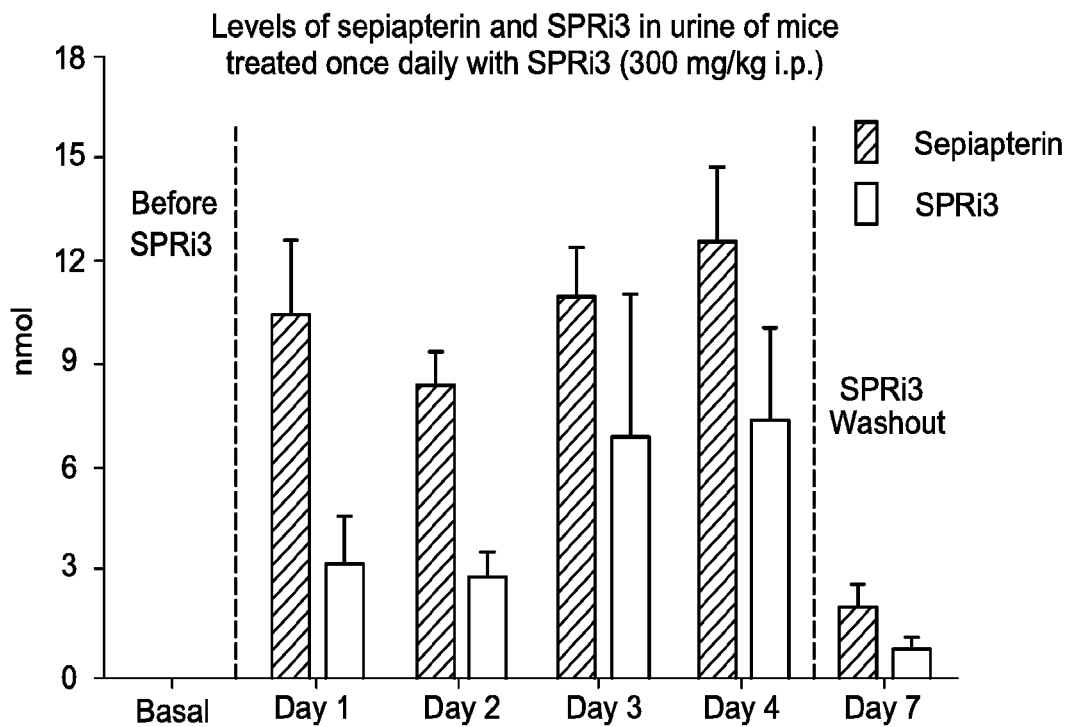
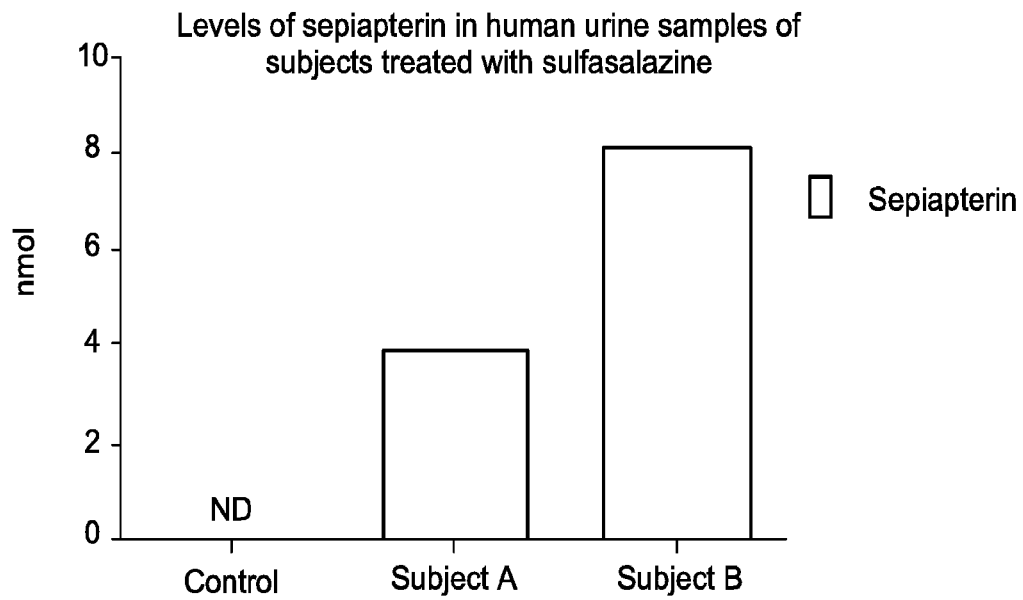
FIG. 9

METHODS AND ASSAYS RELATING TO SEPIAPTERIN REDUCTASE INHIBITION

CROSS-REFERENCE TO RELATED APPLICATIONS

This application is a 35 U.S.C. § 371 National Phase Entry Application of International Application No. PCT/US15/057963 filed Oct. 29, 2015, which designates the U.S. and claims benefit under 35 U.S.C. § 119(e) of U.S. Provisional Application No. 62/073,320 filed Oct. 31, 2014, the contents of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Oct. 23, 2015, is named 701039-082321-PCT SL.txt and is 4,600 bytes in size.

TECHNICAL FIELD

The technology described herein relates to inhibition of sepiapterin reductase, the monitoring of such inhibition, and the treatment of sepiapterin reductase-associated disorders.

BACKGROUND

Sepiapterin reductase (SPR) catalyzes the formation of $BH_4$, which contributes to the perception of pain and the generation of inflammation. Accordingly, inhibition of SPR activity can permit treatment of certain disorders, e.g., chronic pain or pain hypersensitivity, and inflammation.

SUMMARY

The technology described herein is directed to assays and methods of treatment relating to the measurement and/or monitoring of SPR activity and detecting risk of adverse effects by determining sepiapterin levels.

In one aspect, described herein is an assay to identify the presence, degree and/or rate of inhibition of sepiapterin reductase (SPR) by an inhibitor, the assay comprising: contacting a cell with a candidate agent; and measuring the level of sepiapterin; wherein an increased level of sepiapterin indicates the candidate agent is an inhibitor of SPR (SPRi). In some embodiments, an increased level of sepiapterin can be a detectable level of sepiapterin. In some embodiments, the measurement step can comprise performing liquid chromatography coupled to mass spectrometry, fluorescent detection, mass spectroscopy, or ELISA measurement. In some embodiments, the contacting step can comprise contacting an in vitro cell. In some embodiments, the contacting step can comprise contacting an in vitro cell culture. In some embodiments, the contacting step can comprise administering the agent to a subject. In some embodiments, the level of sepiapterin can be the extracellular level of sepiapterin. In some embodiments, the level of sepiapterin can be the intracellular level of sepiapterin. In some embodiments, the intracellular level of sepiapterin can be the level in a cell selected from the group consisting of: a neuron; a white blood cell; a red blood cell; a fibroblast; an epithelial cell; a neural progenitor cell; an embryonic stem cell; and an induced pluripotent stem cell (iPSC). In some embodiments, the cell can be a white blood cell. In some embodiments, the level of extracellular sepiapterin can be the level of sepiapterin in a bodily fluid. In some embodiments, the bodily fluid can be selected from the group consisting of: plasma; blood; cerebrospinal fluid; synovial fluid; saliva; tears; and urine.

In one aspect, described herein is a method of treating a subject with a sepiapterin reductase inhibitor (SPRi), the method comprising: administering a therapeutically effective dose of the sepiapterin reductase inhibitor (SPRi); measuring the level of sepiapterin for monitoring the presence, degree and/or rate of SPR inhibition; administering a further and/or increased dose of the SPRi if the level of sepiapterin is at or lower than a reference range; and ceasing and/or administering a decreased dose of the SPRi if the level of sepiapterin is greater than a reference range. In some embodiments, the further and/or increased dose of the SPRi can be administered if the level of sepiapterin is undetectable.

In one aspect, described herein is a method of monitoring administration of a sepiapterin reductase inhibitor (SPRi) to a subject, the method comprising: administering a dose of the sepiapterin reductase inhibitor (SPRi); measuring the level of sepiapterin at a first time point; and measuring the level of sepiapterin at at least a second time point. In some embodiments, the method can further comprise administering a second dose of the SPRi after the first measuring step and prior to the second measuring step. In some embodiments, a level of sepiapterin at or lower than a reference range can indicate the subject is in need of a further and/or increased dose of the SPRi. In some embodiments, an undetectable level of sepiapterin can indicate the subject is in need of a further and/or increased dose of the SPRi. In some embodiments, a level of sepiapterin greater than a reference range can indicate the subject is in need of ceasing and/or administering a decreased dose of the SPRi. In some embodiments, a level of sepiapterin greater than a reference range where no adverse effects occur due to inhibition of SPR can indicate the subject is in need of ceasing and/or administering a decreased dose of the SPRi. In some embodiments, a level of sepiapterin greater than a reference range where adverse effects occur due to inhibition of SPR can indicate the subject is in need of ceasing and/or administering a decreased dose of the SPRi. In some embodiments, the level of sepiapterin can be the extracellular level of sepiapterin. In some embodiments, the level of extracellular sepiapterin can be the level of sepiapterin in a bodily fluid. In some embodiments, the bodily fluid can be selected from the group consisting of plasma; blood; cerebrospinal fluid; synovial fluid saliva; tears; and urine.

In one aspect, described herein is a method of measuring the central activity and/or penetrance across the blood brain barrier of an SPR inhibitor, the method comprising: measuring the level of sepiapterin in the cerebrospinal fluid; measuring the level of sepiapterin in the blood and/or plasma; calculating the ratio of sepiapterin in the cerebrospinal fluid:blood and/or plasma; wherein a lower ratio indicates a decreased central activity and/or penetrance across the blood brain barrier. In some embodiments, a lower ratio can indicate a decreased risk of central nervous system related adverse effects and a higher ratio indicates increased risk of such adverse effects. In some embodiments, the measurement step can comprise performing a liquid chromatography coupled to mass spectrometry, fluorescent detection or ELISA measurement. In some embodiments, the method can further comprise an initial step of administering an SPR inhibitor to a subject. In some embodiments, the level of sepiapterin can be the extracellular level of sepiapterin. In some embodiments, the level of sepiapterin can be the intracellular level of sepiapterin. In some embodiments, the intracellular level of sepiapterin can be the level in a cell selected from the group consisting of a neuron; a white blood cell; a red blood cell; a fibroblast; an epithelial cell; a neural progenitor cell; an embryonic stem cell; and an iPSC. In some embodiments, the cell can be a white blood cell.

In one aspect, described herein is a method of treating a subject with BH4 or BH2, the method comprising: measuring the level of sepiapterin for monitoring the presence, degree and/or rate of SPR inhibition in a subject; and administering BH4 and/or BH2 to the subject if the level of sepiapterin is greater than a reference level associated with adverse effects due to excessive SPR inhibition and excessively reduced BH4 and BH2 levels. In one aspect, described herein is a method of treating a subject with BH4 or BH2, the method comprising administering BH4 and/or BH2 to a subject determined to have a level of sepiapterin greater than a reference level associated with adverse effects due to excessive SPR inhibition and excessively reduced BH4 and BH2 levels.

In one aspect, described herein is a method of detecting a loss of function mutation in SPR, the method comprising: measuring the level of sepiapterin in a sample; wherein a level of sepiapterin which is increased relative to a reference level indicates the presence of a loss of function mutation of SPR in the sample. In some embodiments, an increased level of sepiapterin can be a detectable level of sepiapterin. In some embodiments, the sample can be a sample obtained from a cell culture. In some embodiments, the sample can be a sample obtained from a subject. In some embodiments, the measurement step can comprise performing liquid chromatography coupled to mass spectrometry, fluorescent detection, mass spectroscopy, or ELISA measurement. In some embodiments, the level of sepiapterin can be the extracellular level of sepiapterin. In some embodiments, the level of sepiapterin can be the intracellular level of sepiapterin. In some embodiments, the intracellular level of sepiapterin can be the level in a cell selected from the group consisting of a neuron; a white blood cell; a red blood cell; a fibroblast; an epithelial cell; a neural progenitor cell; an embryonic stem cell; and an iPSC. In some embodiments, the cell can be a white blood cell. In some embodiments, the level of extracellular sepiapterin can be the level of sepiapterin in a bodily fluid. In some embodiments, the bodily fluid can be selected from the group consisting of plasma; blood; cerebrospinal fluid; synovial fluid; saliva; tears; and urine.

In one aspect, described herein is a method of defining the therapeutic index of an SPRi, the method comprising: administering doses of the sepiapterin reductase inhibitor (SPRi) to a population of subjects; measuring the level of sepiapterin in the subjects for monitoring the presence, degree and/or rate of SPR inhibition; defining the $ED_{50}$ as the dose at which 50% of the population a decrease in pain and/or inflammation; defining the $TD_{50}$ as the dose at which 50% of the population exhibits a level of sepiapterin which is increased relative to a reference level; and calculating the therapeutic index as the ratio between the $TD_{50}$ and the $ED_{50}$. In one aspect, described herein is a method of defining the therapeutic index of an SPRi, the method comprising: administering doses of the sepiapterin reductase inhibitor (SPRi) to a population of subjects; measuring the level of sepiapterin in the subjects for monitoring the presence, degree and/or rate of SPR inhibition; defining the $ED_{50}$ as the dose at which 50% of the population report or experience a decrease in pain and/or inflammation; defining the $TD_{50}$ as the dose at which 50% of the population exhibits a level of sepiapterin which is increased relative to a reference level where adverse effects due to excessive inhibition of SPR are detected; and calculating the therapeutic index as the ratio between the $TD_{50}$ and the $ED_{50}$. In some embodiments, the reference level of sepiapterin can be the level in a subject prior to administration of the SPRi. In some embodiments, an increased level of sepiapterin can be a detectable level of sepiapterin. In some embodiments, the level of sepiapterin can be the extracellular level of sepiapterin. In some embodiments, the level of extracellular sepiapterin can be the level of sepiapterin in a bodily fluid. In some embodiments, the bodily fluid can be selected from the group consisting of plasma; blood; cerebrospinal fluid; synovial fluid saliva; tears; and urine. In some embodiments, the measurement step can comprise performing a mass spectroscopy or ELISA measurement. In some embodiments, the level of sepiapterin can be the intracellular level of sepiapterin. In some embodiments, the intracellular level of sepiapterin can be the level in a cell selected from the group consisting of a neuron; a white blood cell; a red blood cell; a fibroblast; an epithelial cell; a neural progenitor cell; an embryonic stem cell; and an iPSC. In some embodiments, the cell can be a white blood cell.

BRIEF DESCRIPTION OF THE DRAWINGS

FIG. 1A depicts sepiapterin levels in supernatant of mouse dorsal root ganglion neurons exposed to an SPRi (ACS8099/SPRi3) (structure shown in FIG. 1C) for 24 h. FIG. 1B depicts sepiapterin concentration in plasma of mice treated with the SPRi (ACS8099 300 mg/kg; five consecutive days; b.i.d.; i.p.). (ND)=no detectable levels of sepiapterin.

FIG. 9 depicts the measurement of sepiapterin in urine. The upper panel depicts the levels of sepiapterin in urine of mice (n=3-6 per day) treated with a sepiapterin reductase inhibitor (SPRi3; 300mg/kg/day). Sepiapterin was undetectable prior to the SPRi3 treatment (Basal) and levels reduced following washout of the compound. The lower panel depicts a graph of the levels of sepiapterin in samples of urine from humans (subjects A and B) treated with a standard clinical dose of sulfasalazine, an FDA approved SPRi (2 g/day). The control sample was obtained from a human not treated with sulfasalazine and sepiapterin was not detectable (ND).

DETAILED DESCRIPTION

Figure 8A:
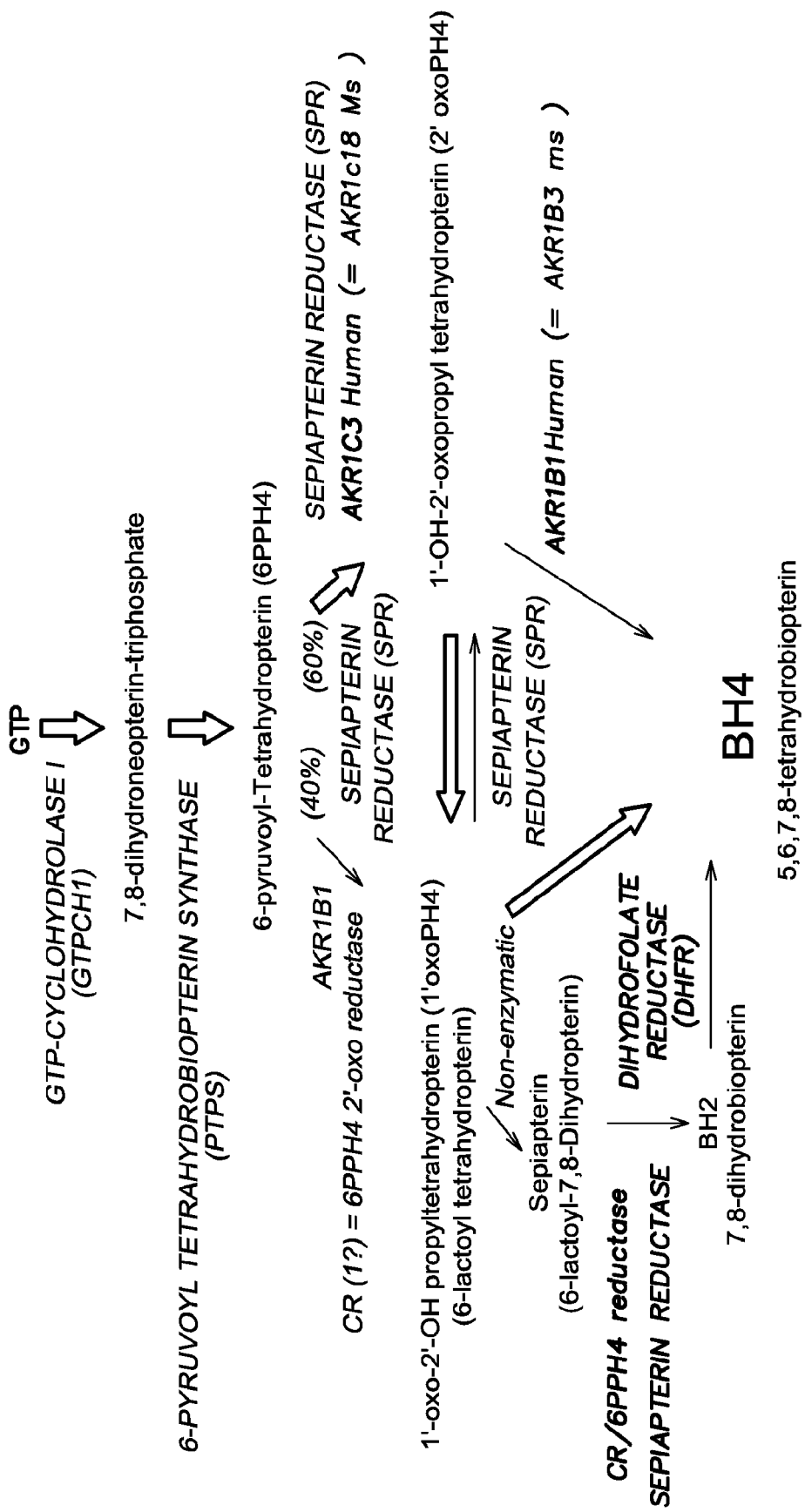
FIGS. 8A-8B depict schematics of the BH4 synthesis pathway under normal conditions (FIG. 8A) or in the case of SPR blockade (FIG. 8B). The importance of the reaction is represented by the thickness of the arrows. Enzymes are in italic. In the absence of SPR the salvage pathway reactions are not as efficient so there is an intracellular accumulation of sepiapterin.
Figure 8B:
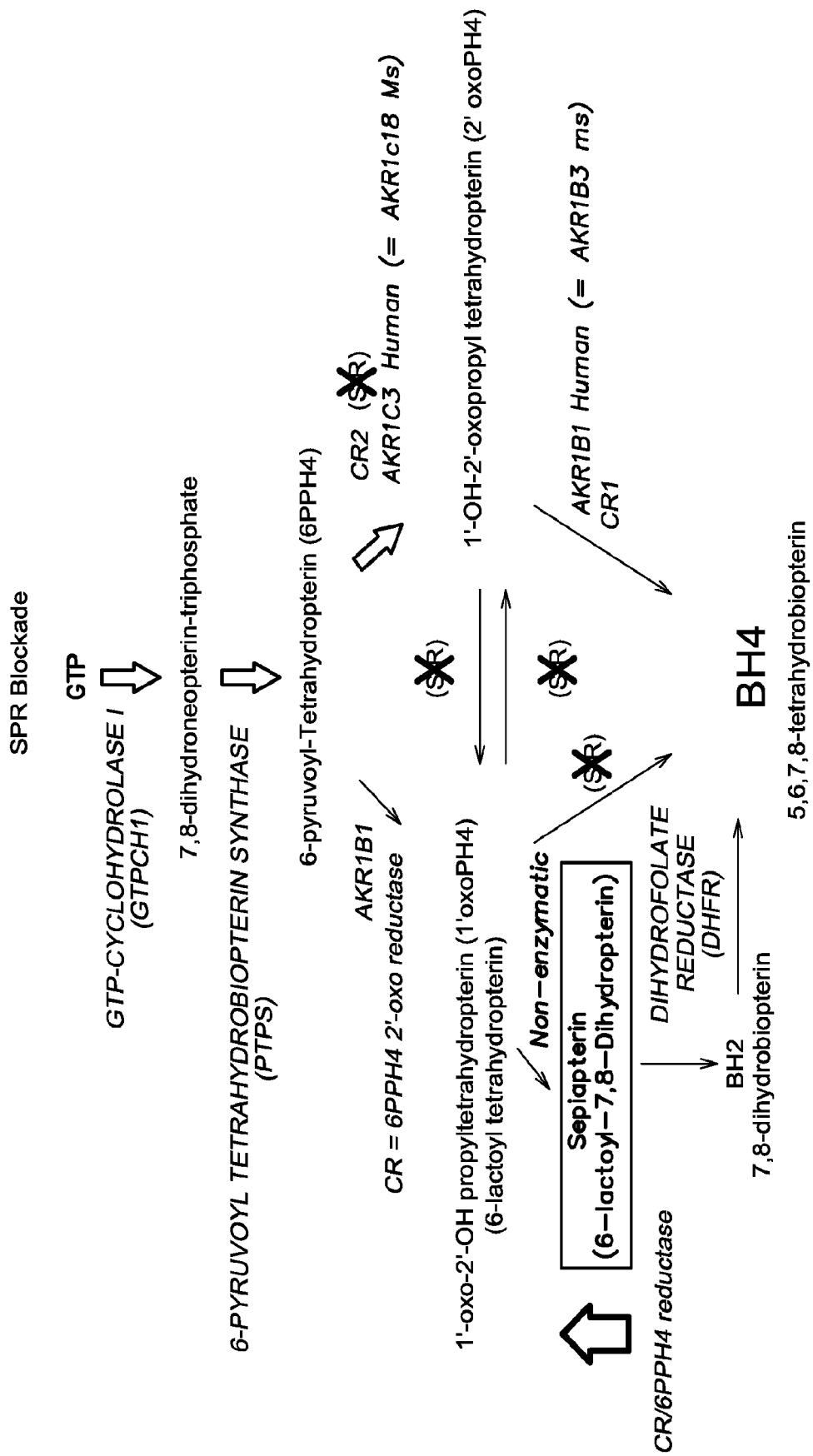
Figure 10:
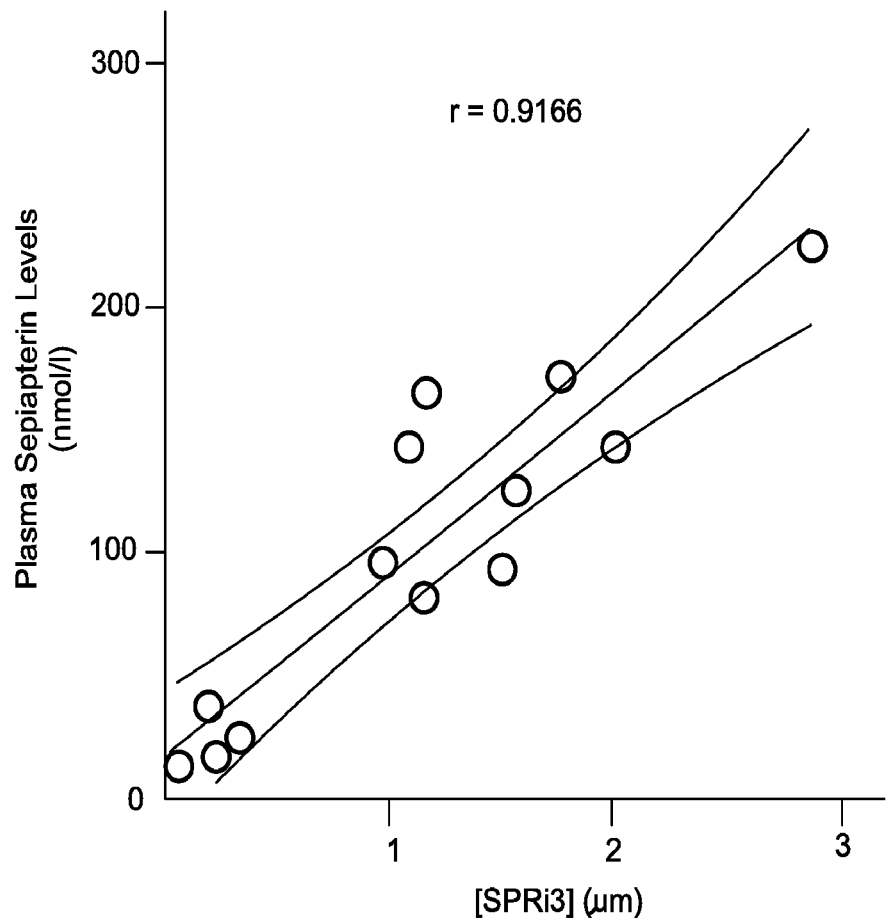
FIG. 10 depicts a graph demonstrating the correlation between plasma sepiapterin and SPRi3 levels.

As described herein, the inventors have determined that sepiapterin levels provide a surprisingly efficacious and unexpected means of measuring and/or monitoring inhibition of or loss of function mutations in sepiapterin reductase (SPR) activity. SPR activity can be modulated to treat a number of conditions, e.g. excessive pain, chronic pain, and/or pain hypersensitivity and acute and chronic inflammatory conditions. SPR is an intracellular enzyme and while levels of its substrate, 6-pyruvoyl-tetrahydrobiopterin, would be expected to rise intracellularly when an inhibitor of SPR is applied, this would not necessarily occur for 6-lactoyl-7,8-dihydropterin (sepiapterin), which can be formed non enzymatically from 6-pyruvoyl-tetrahydrobiopterin (see, e.g. FIGS. 8A-8B). Furthermore, as release processes for sepiapterin have not been identified, sepiapterin could not have been predicted to be increased extracellularly when SPR is inhibited. Measuring sepiapterin levels as a marker of SPRi is an improvement over measuring BH4, as sepiapterin is stable, while BH4 is a metabolite very prone to oxidation. Sepiapterin is an ideal candidate to identify SPR-related inhibition because: i) it is a stable metabolite ii) upon accumulation is not further metabolized, as is the case for 6-pyruvoyl-tetrahydrobiopterin, the SPR substrate in the de novo BH4 pathway; iii) under normal conditions no sepiapterin can be detected in extracellular fluids, giving high sensitivity to the measurement; iv) sepiapterin is only formed in the BH4 salvage pathway, while other metabolites like BH2 and BH4 can be formed by several pathways (see FIGS. 8A-8B for details about the biochemical transformations).

In normal conditions (FIG. 8A), the final steps in the de novo synthesis BH4 pathway are carried by SPR, which converts 6-pyruvoyltetrahydrobiopterin (produced by pyruvoyl tetrahydrobiopterin synthase) to 1'-hydroxy-2'-oxopropyltetrahydropterin, then catalyzes the reaction towards the formation of 1'-oxo-2'-hydroxypropyltetrahydropterin (also known as 6-lactoyl tetrahydropterin) and finally produces BH4. These reactions are all carried out by SPR so under optimal conditions there is no formation/accumulation of sepiapterin; see FIG. 8A). As described herein, in the absence of SPR or when the enzyme is blocked (FIG. 8B), 6-pyruvoyl-tetrahydrobiopterin can be to some extent metabolized into BH4 through alternate enzymatic routes known as the salvage pathway. In the first route, aldose reductase (AKR1B1) and carbonyl reductases (CR) can reduce 6-pyruvoyl-tetrahydrobiopterin into 1'-oxo-2'-hydroxypropyltetrahydropterin.

1'-oxo-2'-hydroxypropyltetrahydropterin is non-enzymatically transformed into sepiapterin (6-lactoyl-7,8-dihydropterin), which is then transformed into 7,8-dihydrobiopterin (BH2) by carbonyl reductases. BH2 is then reduced into BH4 by dihydrofolate reductase. The absence (or blockade) of SPR prevents the direct transformation of 1'-oxo-2'-hydroxypropyltetrahydropterin into BH4. As a result there is a non-enzymatic production of the intermediate sepiapterin from 1'-oxo-2'-hydroxypropyltetrahydropterin/6-lactoyl tetrahydropterin, something that does not normally occur (see FIG. 8B). As described herein, the accumulation of sepiapterin therefore reflects the degree of inhibiton of SPR.

It is possible that both 1'-oxo-2'-hydroxypropyltetrahydropterin and 1'-hydroxy-2'-oxopropyltetrahydropterin accumulate when SPR is inhibited. Those metabolites however are not likely as stable as sepiapterin and therefore less reliable to quantify. BH2 could also accumulate when SPR is blocked. However, BH2 is formed when BH4 is metabolized as a cofactor by monoamine hydroxylases, making its measurement not specific for SPR blockade. The second route of the salvage pathway consists of the aldose reductase AKR1C3 that can reduce 6-pyruvoyl-tetrahydrobiopterin into 1'-hydroxy-2'-oxopropyltetrahydropterin, which is then further reduced into BH4 by AKR1B1 (see FIG. 8B).

Accordingly, provided herein are methods and assays relating to measuring and/or monitoring SPR inhibition and treatment of SPR-related conditions.

As used herein, "sepiapterin reductase" or "SPR" refers to an oxidoreductase that catalyzes the NADPH-dependent reduction of 6-pyruvoyl-tetrahydrobiopterin (de novo synthesis) and sepiapterin 6-lactoyl-7,8-dihydropterin (salvage pathway) to tetrahydrobiopterin (BH$_4$). The sequence of SPR is known for a number of species, e.g. human SPR (NCBI Gene ID NO: 6697; mRNA (NCBI Ref Seq: NM_003124; SEQ ID NO: 1); polypeptide (NCBI Ref Seq: NP_003115; SEQ ID NO: 2).

As used herein, "sepiapterin" refers to a compound having the structure of Formula I Formula I

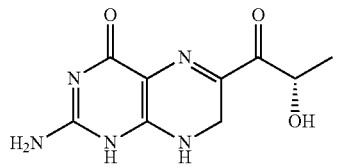

As used herein, the term "inhibitor" refers to an agent which can decrease the expression and/or activity of the targeted expression product (e.g. mRNA encoding the target or a target polypeptide), e.g. by at least 10% or more, e.g. by 10% or more, 50% or more, 70% or more, 80% or more, 90% or more, 95% or more, or 98% or more. The efficacy of an inhibitor, e.g. its ability to decrease the level and/or activity of the target, can be determined, e.g. by measuring the level of an expression product of and/or the activity of the target. Methods for measuring the level of a given mRNA and/or polypeptide are known to one of skill in the art, e.g. RTPCR can be used to determine the level of RNA and Western blotting with an antibody can be used to determine the level of a polypeptide. The activity of a target can be determined using methods known in the art and described herein, e.g. transcriptional activity assays. In some embodiments, the inhibitor can be an inhibitory nucleic acid; an aptamer; an antibody reagent; an antibody; or a small molecule. Non-limiting examples of SPR inhibitors (SPRi's) can include sulfapyridine; ACS8099/SPRi3; N-Acetylserotonin; and several sulfa drugs including sulfasalazine (see, e.g., Haruki Science 2013 340:987-991 and International Patent Publications WO 2011/047156 and WO 2011/035009; each of which is incorporated by reference herein in its entirety).

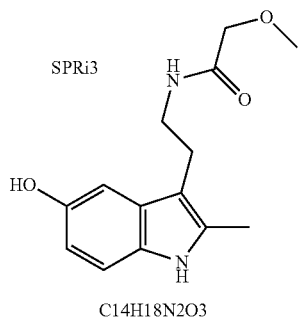

C14H18N2O3

In one aspect, described herein is an assay to identify the presence, degree and/or rate of inhibition of SPR by an inhibitor, the assay comprising contacting a cell with a candidate agent and measuring the level of sepiapterin; wherein an increased level of sepiapterin indicates the candidate agent is an SPRi.

The level of sepiapterin can be measured by any means known in the art. Exemplary methods can include enzyme linked immunosorbent assay; chemiluminescent immunosorbent assay; electrochemiluminescent immunosorbent assay; fluorescent immunosorbent assay; dye linked immunosorbent assay; immunoturbidimetric assay; immunonephelometric assay; dye-based photometric assay; western blot; immunoprecipitation; radioimmunological assay (RIA); radioimmunometric assay; immunofluorescence assay; mass spectroscopy; liquid chromatography tandem mass spectroscopy; and high-pressure liquid chromatography. In some embodiments, the level of sepiapterin can be determined by mass spectroscopy. In some embodiments, the level of sepiapterin can be determined by liquid chromatography coupled to mass spectrometry or fluorescent detection. In some embodiments, the level of sepiapterin can be determined by ELISA.

In some embodiments, the level of sepiapterin can be the extracellular level of sepiapterin. In some embodiments, the level of sepiapterin can be the intracellular level of sepiapterin, e.g. the level in white blood cells. In some embodiments, the level of sepiapterin can be the level of sepiapterin in a bodily fluid. In some embodiments, the bodily fluid can be selected from the group consisting of: plasma; blood; cerebrospinal fluid; synovial fluid; saliva; tears; and urine. In some embodiments, the bodily fluid is urine.

In some embodiments, the cell which is contacted with the SPRi can be an in vitro cell, e.g. the assay can be an in vitro cell assay. In some embodiments, the cell which is contacted with the SPRi can be an in vitro cell culture, e.g. the assay can be an in vitro cell assay. The cell can be an isolated cultured cell (e.g. an isolated primary cell or a cultured cell line) or part of a tissue (natural or artificial). In some embodiments, the cell can be a neuron, a white blood cell, red blood cell, fibroblasts, epithelial cells, neural progenitor cell, embryonic stem cell/iPSC or any cell derived from these stem cells or a progenitor of any of the proceeding cell types (e.g. a stem cell, IPS cell, or the like).

In some embodiments, the cell which is contacted with the SPRi can be present in a subject, e.g., the contacting step can comprise administering the agent to a subject. In some embodiments, the subject can be a subject in need of treatment for SPR-associated disorders, e.g., acute or chronic pain, pain hypersensitivity, neuropathic pain, inflammatory pain, nociceptive pain, inflammation (including, e.g., arthritis and inflammatory bowel disease), asthma and allergic inflammatory conditions, or autoimmune diseases that are due or contributed to by increased BH4 synthesis and where a reduction in BH4 levels produced by an SPRi produces benefit. In some embodiments, the subject can be a human. In some embodiments, the subject can be a mammal. The administration can be according to any method known in the art. In some embodiments, the administration can be via injection or intravenous, intranasal, inhaled, intraocular, topical or oral.

In one aspect, described herein is a method of treating a subject with an SPRi, the method comprising administering a therapeutically effective dose of the SPRi, measuring the level of sepiapterin (e.g. monitoring the presence, degree and/or rate of SPR inhibition), administering a further and/or increased dose of the SPRi if the level of sepiapterin is at or lower than a reference range; and ceasing and/or administering a decreased dose of the SPRi if the level of sepiapterin is greater than a reference range. In some embodiments, described herein is a method of treating a subject with an SPRi, the method comprising administering a therapeutically effective dose of the SPRi, measuring the level of sepiapterin (e.g. monitoring the presence, degree and/or rate of SPR inhibition), administering a further and/or increased dose of the SPRi if the level of sepiapterin is at or lower than a reference range (e.g. is undetectable); and ceasing and/or administering a decreased dose of the SPRi if the level of sepiapterin is greater than a reference range (e.g., is detectable). In some embodiments, administering a decreased dose of the SPRi can be administered if the level of sepiapterin is greater than a reference range associated with adverse effects due to excessive decrease in BH4 levels.

Some subjects, e.g., those with a loss of function mutation in SPR and/or those receiving treatment with a sulfa drug, may have decreased SPR activity such that treatment with an SPRi would be contraindicated. Accordingly, in one aspect, provided herein is a method of treating a subject with a sepiapterin reductase inhibitor (SPRi), the method comprising: measuring the level of sepiapterin in a sample obtained from a subject; administering a therapeutically effective dose of the sepiapterin reductase inhibitor (SPRi) if the level of sepiapterin is at or lower than a reference range; and not administering a SPRi if the level of sepiapterin is greater than a reference range. In some embodiments, the subject is a subject who has received or is receiving treatment with a sulfa drug.

In some embodiments, a level of sepiapterin can be greater than a reference level or range if it is statistically significantly greater than the reference. In healthy subjects, (e.g., those not having or diagnosed as having acute and chronic pain, pain hypersensitivity, neuropathic pain, inflammatory pain, nociceptive pain or for inflammation including arthritis and inflammatory bowel disease, asthma and allergic inflammatory conditions, or autoimmune diseases) the level of sepiapterin can be undetectable, e.g., there is no sepiapterin present in such subjects. Accordingly, in some embodiments, a level of sepiapterin can be greater than a reference level or range if it is detectable. In some embodiments, a level of sepiapterin can be greater than a healthy reference level or range if it is 2×or greater, e.g. 3×, 4×, 5× or greater than the reference.

In some embodiments, a level of sepiapterin can be less than a reference level if it is statistically significantly less than the reference. In some embodiments, a level of sepiapterin can be less than a reference level or range if it is 50% or less, e.g. 40%, 30%, 20%, 10% or less of the reference. In some embodiments, a level which is lower than a reference range can be a level that is undetectable.

In some embodiments, a reference level and/or range can be the level and/or range obtained with a sample obtained from a healthy subject, i.e. a subject not having or diagnosed as having an SPR-associated disorder (e.g. chronic pain or inflammation that responds to an SPRi). In some embodiments, the reference level and/or range can be the level and/or range obtained for a population of healthy subjects. In some embodiments, the reference level and/or range can be the level and/or range obtained for the subject at an earlier date, e.g. before chronic pain symptoms were evident or before an increase in symptoms.

In some embodiments, a reference level and/or range can be the level and/or range obtained with a sample obtained from subjects with an SPR-associated disorder (e.g. chronic pain or inflammation that responds to a SPRi or a mutation of SPR) and/or from subjects given different doses of an SPRi. In some embodiments, the reference level and/or range can be the levels and/or ranges obtained for subjects given different doses of a SPRi who did or did not develop adverse effects. In some embodiments, the level(s) and/or range(s) of sepiapterin levels may define risks of developing adverse effects due to excessive reduction of BH4 synthesis; e.g., wherein low levels indicate inhibition of SPR but with no adverse effects and wherein high levels of sepiapterin indicate excessive inhibition resulting in decreased BH4 and increased risk of adverse effects.

In some embodiments, the methods and assays described herein can comprise measuring the level of sepiapterin in a test sample, e.g. a sample obtained from a subject. The term "test sample" as used herein denotes a sample taken or isolated from a biological organism, e.g., blood, plasma, cerebrospinal fluid, synovial fluid, urine, tears or any other fluid or cell or tissue sample obtained from a subject. The term "test sample" also includes untreated or pretreated (or pre-processed) biological samples. A test sample can contain cells from subject, but the term can also refer to non-cellular biological material, such as non-cellular fractions. Samples can also include, e.g., frozen tissue.

The test sample can be obtained by removing a sample (e.g. of cells) from a subject, but can also be accomplished by using previously isolated samples (e.g. isolated at a prior timepoint and isolated by the same or another person). In addition, the test sample can be freshly collected or a previously collected sample. In some embodiments, the test sample can be an untreated test sample. As used herein, the phrase "untreated test sample" refers to a test sample that has not had any prior sample pre-treatment except for dilution and/or suspension in a solution. Exemplary methods for treating a test sample include, but are not limited to, centrifugation, filtration, sonication, homogenization, heating, freezing and thawing, and combinations thereof. In some embodiments, the test sample can be a frozen test sample, e.g., a frozen tissue. The frozen sample can be thawed before employing methods, assays and systems described herein. After thawing, a frozen sample can be centrifuged before being subjected to methods, assays and systems described herein. In some embodiments, the test sample is a clarified test sample, for example, by centrifugation and collection of a supernatant comprising the clarified test sample. In some embodiments, a test sample can be a pre-processed test sample, for example, supernatant or filtrate resulting from a treatment selected from the group consisting of centrifugation, filtration, sonication, homogenization, lysis, thawing, amplification, purification, restriction enzyme digestion ligation and any combinations thereof.

In some embodiments, the test sample can be treated with a chemical and/or biological reagent. Chemical and/or biological reagents can be employed to protect and/or maintain the stability of the sample, including biomolecules (e.g., nucleic acid and protein) therein, during processing. One exemplary reagent is a protease inhibitor, which is generally used to protect or maintain the stability of protein during processing. In addition, or alternatively, chemical and/or biological reagents can be employed to release nucleic acid or protein from the sample. The skilled artisan is well aware of methods and processes appropriate for pre-processing of biological samples required for determination of expression of gene products as described herein.

In one aspect, described herein is a method of monitoring administration of an SPRi to a subject, the method comprising: administering a dose of the SPRi; measuring the level of sepiapterin at a first time point; and measuring the level of sepiapterin at at least a second time point. In some embodiments, the method further comprises administering a second dose of the SPRi after the first measuring step and prior to the second measuring step. In some embodiments, a level of sepiapterin not higher than a reference range indicates the subject is in need of a further and/or increased dose of the SPRi and/or or that further SPRi is unlikely to produce adverse effects. In some embodiments, an undetectable level of sepiapterin indicates the subject is in need of a further and/or increased dose of the SPRi and/or that further SPRi is unlikely to produce adverse effects. In some embodiments, a level of sepiapterin that is increasing after each administration and/or greater than a reference range indicates the subject is in need of ceasing and/or administering a decreased dose of the SPRi, e.g., to avoid generation of adverse effects.

The assays and methods of measuring SPR activity as described herein can permit determining the relative activity of SPR (in the presence or absence of an SPRi) within and without the central nervous system, e.g. measuring the ability of an SPRi to cross the blood-brain barrier (i.e., penetrance) and/or to inhibit SPR within the central nervous system. In one aspect, described herein is a method of measuring the central activity and/or penetrance across the blood brain barrier of an SPRi, the method comprising: measuring the level of sepiapterin in the cerebrospinal fluid; measuring the level of sepiapterin in the blood and/or plasma; calculating the ratio of sepiapterin in the cerebrospinal fluid:blood and/or plasma; wherein a lower ratio indicates a decreased central activity and/or penetrance across the blood brain barrier. Cerebrospinal fluid can be collected and/or sampled by any means known in the art, e.g. by lumbar puncture, cisternal puncture, and/or ventricular puncture. In some embodiments, a lower ratio indicates a decreased risk of central nervous system related adverse effects (e.g., altered consciousness, dizziness, seizures, muscle spasm, fatigue, sedation, lethargy, and/or personality alterations). In some embodiments, the method can further comprise an initial step of administering an SPRi to a subject.

In one aspect, described herein is a method of treating a subject with $BH_4$ or $BH_2$, the method comprising: measuring the level of sepiapterin for monitoring the presence, degree and/or rate of SPR inhibition as described above herein; and administering $BH_4$ and/or $BH_2$ if the level of sepiapterin is greater than levels associated with adverse effects, e.g., as defined by reference levels from patients given ranges of doses of SPRi. In some embodiments, the levels of sepiapterin can be used to monitor the degree of inhibition of SPR and/or to detect thresholds where the inhibition is excessive and risks development of adverse effects. In some embodiments, sepiapterin levels can define the therapeutic index of SPR inhibitors, the safe range of doses that produce efficacy in SPR-realted conditions without adverse effects.

As used herein, "$BH_4$" or "tetrahydrobiopterin" refers to a compound having the structure of Formula II:

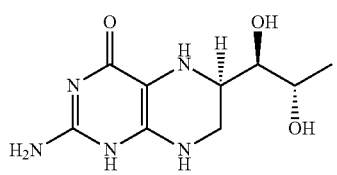

Formula II

BH4 is also referred to in the art as THB, Kuvan™, or sapropterin.

As used herein, "$BH_2$" or "7,8-dihydrobiopterin" refers to a compound having the structure of Formula III:

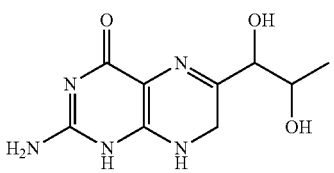

Formula III

In one aspect, described herein is a method of defining the therapeutic index of a SPRi, the method comprising administering doses of the sepiapterin reductase inhibitor (SPRi) to a population of subjects; measuring the level of sepiapterin in the subjects for monitoring the presence, degree and/or rate of SPR inhibition; defining the $ED_{50}$ as the dose at which 50% of the population a decrease in pain and/or inflammation; defining the $TD_{50}$ as the dose at which 50% of the population exhibits a level of sepiapterin which is increased relative to a reference level; and calculating the therapeutic index as the ratio between the $TD_{50}$ and the $ED_{50}$. In one aspect, described herein is a method of defining the therapeutic index of a SPRi, the method comprising administering doses of the sepiapterin reductase inhibitor (SPRi) to a population of subjects; measuring the level of sepiapterin in the subjects for monitoring the presence, degree and/or rate of SPR inhibition; defining the $ED_{50}$ as the dose at which 50% of the population a decrease in pain and/or inflammation; defining the $TD_{50}$ as the dose at which 50% of the population exhibits a level of sepiapterin which is increased relative to a reference level where either signs of toxicity are evident or undesired metabolic changes/adverse effects occur, and calculating the therapeutic index as the ratio between the $TD_{50}$ and the $ED_{50}$. In some embodiments, the reference level of sepiapterin is the level in a subject prior to administration of the SPRi. In some embodiments, the reference level of sepiapterin is the level in a healthy subject or a population of healthy subjects. In some embodiments, the reference level of sepiapterin is the level in a subject or a populatin of subjects who do not display adverse effects after administration of an SPRi. In some embodiments, an increased level of sepiapterin is a detectable level of sepiapterin.

In some embodiments, the methods described herein relate to treating a subject having or diagnosed as having an SPR-associated disorder, e.g., chronic pain or pain hypersensitivity and inflammation with, e.g., a SPRi. Subjects having chronic pain can be identified by a physician using current methods of diagnosing chronic pain. Symptoms and/or complications of chronic pain which characterize these conditions and aid in diagnosis are well known in the art and include but are not limited to, pain, depression, and fatigue.

The compositions and methods described herein can be administered to a subject having or diagnosed as having an SPR-associated disorder. In some embodiments, the methods described herein comprise administering an effective amount of compositions described herein, e.g. a SPRi to a subject in order to alleviate a symptom of an SPR-associated disorder. As used herein, "alleviating a symptom of a disorder" is ameliorating any condition or symptom associated with the disorder. As compared with an equivalent untreated control, such reduction is by at least 5%, 10%, 20%, 40%, 50%, 60%, 80%, 90%, 95%, 99% or more as measured by any standard technique. A variety of means for administering the compositions described herein to subjects are known to those of skill in the art. Such methods can include, but are not limited to oral, parenteral, intravenous, intramuscular, subcutaneous, transdermal, airway (aerosol), pulmonary, cutaneous, topical, or injection administration. Administration can be local or systemic.

The term "effective amount" as used herein refers to the amount of a compound needed to alleviate at least one or more symptoms of the disease or disorder, and relates to a sufficient amount of pharmacological composition to provide the desired effect. The term "therapeutically effective amount" therefore refers to an amount of a compound that is sufficient to provide a particular effect when administered to a typical subject. An effective amount as used herein, in various contexts, would also include an amount sufficient to delay the development of a symptom of the disease, alter the course of a symptom disease (for example but not limited to, slowing the progression of a symptom of the disease), or reverse a symptom of the disease. Thus, it is not generally practicable to specify an exact "effective amount". However, for any given case, an appropriate "effective amount" can be determined by one of ordinary skill in the art using only routine experimentation.

Effective amounts, toxicity, unwanted on-target effects and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized. The dose ratio between toxic and therapeutic effects is the therapeutic index and can be expressed as the ratio LD50/ED50. Compositions and methods that exhibit large therapeutic indices are preferred. A therapeutically effective dose can be estimated initially from cell culture assays. Also, a dose can be formulated in animal models to achieve a circulating plasma concentration range that includes the IC50 (i.e., the concentration of a compound which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay, e.g., assay for SPR inhibition, reduction in BH4 levels, among others. The dosage can be determined by a physician and adjusted, as necessary, to suit observed effects of the treatment.

The methods described herein can further comprise administering a second agent and/or treatment to the subject, e.g. as part of a combinatorial therapy. By way of non-limiting example, if a subject is to be treated for pain or inflammation according to the methods described herein, the subject can also be administered a second agent and/or treatment known to be beneficial for subjects suffering from pain or inflammation. Examples of such agents and/or treatments include, but are not limited to, non-steroidal anti-inflammatory drugs (NSAIDs—such as aspirin, ibuprofen, or naproxen); corticosteroids, including glucocorticoids (e.g. cortisol, prednisone, prednisolone, methylprednisolone, dexamethasone, betamethasone, triamcinolone, and beclometasone); methotrexate; sulfasalazine; gabapentin; pregabalin; tricyclic antidepressants; duloxetine; leflunomide; anti-TNF medications; methotrexate or other dihrofolate reductase inhibitors, cyclophosphamide; pro-resolving drugs; mycophenolate; or opiates (e.g. endorphins, enkephalins, and dynorphin), steroids, analgesics, barbiturates, oxycodone, morphine, lidocaine, and the like.

In certain embodiments, an effective dose of a composition comprising, e.g., an SPRi, as described herein can be administered to a patient once. In certain embodiments, an effective dose of a composition can be administered to a patient repeatedly. For systemic administration, subjects can be administered a therapeutic amount of a composition, such as, e.g. 0.1 mg/kg, 0.5 mg/kg, 1.0 mg/kg, 2.0 mg/kg, 2.5 mg/kg, 5 mg/kg, 10 mg/kg, 15 mg/kg, 20 mg/kg, 25 mg/kg, 30 mg/kg, 40 mg/kg, 50 mg/kg, or more.

In some embodiments, after an initial treatment regimen, the treatments can be administered on a less frequent basis. For example, after treatment biweekly for three months, treatment can be repeated once per month, for six months or a year or longer. Treatment according to the methods described herein can reduce levels of a marker or symptom of a condition, e.g. by at least 10%, at least 15%, at least 20%, at least 25%, at least 30%, at least 40%, at least 50%, at least 60%, at least 70%, at least 80% or at least 90% or more.

The dosage of a composition as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment, or make other alterations to the treatment regimen. The dosing schedule can vary from once a week to daily depending on a number of clinical factors, such as the subject's sensitivity to the treatment. The desired dose or amount of activation can be administered at one time or divided into subdoses, e.g., 2-4 subdoses and administered over a period of time, e.g., at appropriate intervals through the day or other appropriate schedule. In some embodiments, administration can be chronic, e.g., one or more doses and/or treatments daily over a period of weeks or months. Examples of dosing and/or treatment schedules are administration daily, twice daily, three times daily or four or more times daily over a period of 1 week, 2 weeks, 3 weeks, 4 weeks, 1 month, 2 months, 3 months, 4 months, 5 months, or 6 months, or more. A composition can be administered over a period of time, such as over a 5 minute, 10 minute, 15 minute, 20 minute, or 25 minute period.

The dosage ranges for the administration of, e.g., an SPRi, according to the methods described herein depend upon, for example, the form of the compound, its potency, and the extent to which symptoms, markers, or indicators of a condition described herein are desired to be reduced, for example the percentage reduction desired for symptoms. The dosage should not be so large as to cause adverse side effects. Generally, the dosage will vary with the age, condition, and sex of the patient and can be determined by one of skill in the art. The dosage can also be adjusted by the individual physician in the event of any complication.

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

For convenience, certain terms employed herein, in the specification, examples and appended claims are collected here.

The terms "decrease", "reduced", "reduction", or "inhibit" are all used herein to mean a decrease by a statistically significant amount. In some embodiments, "reduce,""reduction" or "decrease" or "inhibit" typically means a decrease by at least 10% as compared to a reference level (e.g. the absence of a given treatment) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99% , or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased", "increase", "enhance", or "activate" are all used herein to mean an increase by a statically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, an "increase" is a statistically significant increase in such level.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of, e.g. chronic pain. A subject can be male or female.

A subject can be one who has been previously diagnosed with or identified as suffering from or having a condition in need of treatment (e.g. chronic pain) or one or more complications related to such a condition, and optionally, have already undergone treatment for the condition or the one or more complications related to the condition. Alternatively, a subject can also be one who has not been previously diagnosed as having the condition (e.g. chronic pain) or one or more complications related to the condition. For example, a subject can be one who exhibits one or more risk factors for the condition or one or more complications related to the condition or a subject who does not exhibit risk factors.

A "subject in need" of treatment for a particular condition can be a subject having that condition, diagnosed as having that condition, or at risk of developing that condition.

The term "isolated" or "partially purified" as used herein refers to an agent separated from at least one other component (e.g., nucleic acid or polypeptide) that is present with the agent as found in its natural source and/or that would be present with the agent when expressed by a cell. For example, a chemically synthesized polypeptide or one synthesized using in vitro transcription/translation is considered "isolated."

As used herein, "contacting" refers to any suitable means for delivering, or exposing, an agent to at least one complex, enzyme, or cell. Exemplary delivery methods include, but are not limited to, direct delivery to cell culture medium, perfusion, injection, or other delivery method well known to one skilled in the art.

As used herein, the term "detecting" refers to observing a signal from, e.g. a probe, label, or target molecule to indicate the presence of an analyte in a sample. Any method known in the art for detecting a particular label moiety can be used for detection. Exemplary detection methods include, but are not limited to, spectroscopic, fluorescent, photochemical, biochemical, immunochemical, electrical, optical or chemical methods.

As used herein, the terms "compound" or "agent" are used interchangeably and refer to molecules and/or compositions including, but not limited to chemical compounds and mixtures of chemical compounds, e.g., small organic or inorganic molecules; saccharines; oligosaccharides; polysaccharides; biological macromolecules, e.g., peptides, proteins, and peptide analogs and derivatives; peptidomimetics; nucleic acids; nucleic acid analogs and derivatives; extracts made from biological materials such as bacteria, plants, fungi, or animal cells or tissues; naturally occurring or synthetic compositions; peptides; aptamers; and antibodies and intrabodies, or fragments thereof.

As used herein, the terms "candidate compound" or "candidate agent" refer to a compound or agent and/or compositions thereof that are to be screened for their ability to, e.g., inhibit SPR. Candidate compounds and/or agents can be produced recombinantly using methods well known to those of skill in the art (see Sambrook et al., Molecular Cloning: A Laboratory Manual (2 ed.), Cold Spring Harbor Laboratory Press, Cold Spring Harbor, N.Y., USA (1989)) or synthesized. Candidate compounds and agents can be screened for their ability to inhibit SPR, e.g. in vitro or in vivo. In one embodiment, candidate agents are screened using the assays described above herein. Candidate agents are typically first screened for activity in vitro and those candidate agents with activity are identified. In vivo assays can then be conducted on the identified agents.

Compounds can be tested at any concentration that can modulate expression or protein activity relative to a control over an appropriate time period. In some embodiments, compounds are tested at concentrations in the range of about 0.1 nM to about 1000 mM. In one embodiment, the compound is tested in the range of about 0.1 µM to about 20 µM, about 0.1 µM to about 10 µM, or about 0.1 µM to about 5 µM. In one embodiment, compounds are tested at 1 µM. Depending upon the particular embodiment being practiced, the test compounds can be provided free in solution, or may be attached to a carrier, or a solid support, e.g., beads. A number of suitable solid supports may be employed for immobilization of the test compounds. Examples of suitable solid supports include agarose, cellulose, dextran (commercially available as, i.e., Sephadex, Sepharose) carboxymethyl cellulose, polystyrene, polyethylene glycol (PEG), filter paper, nitrocellulose, ion exchange resins, plastic films, polyaminemethylvinylether maleic acid copolymer, glass beads, amino acid copolymer, ethylene-maleic acid copolymer, nylon, silk, etc. Additionally, for the methods described herein, test compounds may be screened individually, or in groups. Group screening is particularly useful where hit rates for effective test compounds are expected to be low such that one would not expect more than one positive result for a given group.

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable nucleic acid molecules are DNA, including genomic DNA or cDNA. Other suitable nucleic acid molecules are RNA, including mRNA.

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder, e.g. chronic pain. The term "treating" includes reducing or alleviating at least one adverse effect or symptom of a condition, disease or disorder associated with SPR, e.g., chronic pain or inflammation. Treatment is generally "effective" if one or more symptoms or clinical markers are changed, in the case of SPR inhibition, an increase in sepiapterin. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

As used herein, the term "pharmaceutical composition" refers to the active agent in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "administering," refers to the placement of a compound as disclosed herein into a subject by a method or route, which results in at least partial delivery of the agent at a desired site. Pharmaceutical compositions comprising the compounds disclosed herein can be administered by any appropriate route, which results in an effective treatment in the subject.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean ±1%.

As used herein the term "comprising" or "comprises" is used in reference to compositions, methods, and respective component(s) thereof, that are essential to the method or composition, yet open to the inclusion of unspecified elements, whether essential or not.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Definitions of common terms in cell biology and molecular biology can be found in "The Merck Manual of Diagnosis and Therapy", 19th Edition, published by Merck Research Laboratories, 2006 (ISBN 0-911910-19-0); Robert S. Porter et al. (eds.), The Encyclopedia of Molecular Biology, published by Blackwell Science Ltd., 1994 (ISBN 0-632-02182-9); Benjamin Lewin, Genes X, published by Jones & Bartlett Publishing, 2009 (ISBN-10: 0763766321); Kendrew et al. (eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

Unless otherwise stated, the present invention was performed using standard procedures, as described, for example in Sambrook et al., Molecular Cloning: A Laboratory Manual (4 ed.), Cold Spring Harbor Laboratory Press, Cold Spring Harbor, N.Y., USA (2012); Davis et al., Basic Methods in Molecular Biology, Elsevier Science Publishing, Inc., New York, USA (1995); or Methods in Enzymology: Guide to Molecular Cloning Techniques Vol.152, S. L. Berger and A. R. Kimmel Eds., Academic Press Inc., San Diego, USA (1987); Current Protocols in Protein Science (CPPS) (John E. Coligan, et. al., ed., John Wiley and Sons, Inc.), Current Protocols in Cell Biology (CPCB) (Juan S. Bonifacino et. al. ed., John Wiley and Sons, Inc.), and Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998) which are all incorporated by reference herein in their entireties.

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting.

Some embodiments of the technology described herein can be defined according to any of the following numbered paragraphs:

1. An assay to identify the presence, degree and/or rate of inhibition of sepiapterin reductase (SPR) by an inhibitor, the assay comprising:
   contacting a cell with a candidate agent; and
   measuring the level of sepiapterin;
   wherein an increased level of sepiapterin indicates the candidate agent is an inhibitor of SPR.
2. The assay of paragraph 1, wherein an increased level of sepiapterin is a detectable level of sepiapterin.
3. The assay of any of paragraphs 1-2, wherein the measurement step comprises performing a liquid chromatography coupled to mass spectrometry, fluorescent detection, mass spectroscopy, or ELISA measurement.
4. The assay of any of paragraphs 1-3, wherein the contacting step comprises contacting an in vitro cell.
5. The assay of any of paragraphs 1-4, wherein the contacting step comprises administering the agent to a subject.
6. The assay of any of paragraphs 1-5, wherein the level of sepiapterin is the extracellular level of sepiapterin.
7. The assay of any of paragraphs 1-6, wherein the level of sepiapterin is the intracellular level of sepiapterin.
8. The assay of paragraph 7, wherein the intracellular level of sepiapterin is the level in a cell selected from the group consisting of:
   a neuron; a white blood cell; a red blood cell; a fibroblast; an epithelial cell; a neural progenitor cell; an embryonic stem cell; and an iPSC.
9. The assay of any of paragraphs 7-8, wherein the cell is a white blood cell.
10. The assay of paragraph 6, wherein the level of extracellular sepiapterin is the level of sepiapterin in a bodily fluid.
11. The assay of paragraph 10, wherein the bodily fluid is selected from the group consisting of:
    plasma; blood; cerebrospinal fluid; synovial fluid; saliva; tears; and urine.
12. The assay of paragraph 11, wherein the bodily fluid is urine.
13. A method of treating a subject with a sepiapterin reductase inhibitor (SPRi), the method comprising:
    administering a therapeutically effective dose of the sepiapterin reductase inhibitor (SPRi);
    measuring the level of sepiapterin for monitoring the presence, degree and/or rate of SPR inhibition;
    administering a further and/or increased dose of the SPRi if the level of sepiapterin is at or lower than a reference range; and
    ceasing and/or administering a decreased dose of the SPRi if the level of sepiapterin is greater than a reference range.
14. The method of paragraph 13, wherein the further and/or increased dose of the SPRi is administered if the level of sepiapterin is undetectable.
15. A method of monitoring administration of a sepiapterin reductase inhibitor (SPRi) to a subject, the method comprising:
    administering a dose of the sepiapterin reductase inhibitor (SPRi);
    measuring the level of sepiapterin at a first time point; and
    measuring the level of sepiapterin at at least a second time point.
16. The method of paragraph 15, wherein the method further comprises administering a second dose of the SPRi after the first measuring step and prior to the second measuring step.
17. The method of any of paragraphs 15-16, wherein a level of sepiapterin at or lower than a reference range indicates the subject is in need of a further and/or increased dose of the SPRi.
18. The method of any of paragraphs 15-17, wherein an undetectable level of sepiapterin indicates the subject is in need of a further and/or increased dose of the SPRi.
19. The method of any of paragraphs 15-18, wherein an undetectable level of sepiapterin indicates the subject has not taken the medication.
20. The method of any of paragraphs 15-19, wherein a level of sepiapterin greater than a reference range indicates the subject is in need of ceasing and/or administering a decreased dose of the SPRi.
21. The method of any of paragraphs 15-20, wherein a level of sepiapterin greater than a reference range where no adverse effects occur due to inhibition of SPR indicates the subject is in need of ceasing and/or administering a decreased dose of the SPRi.
22. The method of any of paragraphs 15-20, wherein a level of sepiapterin greater than a reference range where adverse effects occur due to inhibition of SPR indicates the subject is in need of ceasing and/or administering a decreased dose of the SPRi.

23. The method of any of paragraphs 15-22, wherein the level of sepiapterin is the extracellular level of sepiapterin.

24. The method of paragraph 23, wherein the level of extracellular sepiapterin is the level of sepiapterin in a bodily fluid.

25. The method of paragraph 24, wherein the bodily fluid is selected from the group consisting of:
plasma; blood; cerebrospinal fluid; synovial fluid saliva; tears; and urine.

26. The method of paragraph 25, wherein the bodily fluid is urine.

27. A method of measuring the central activity and/or penetrance across the blood brain barrier of an SPR inhibitor, the method comprising:
measuring the level of sepiapterin in the cerebrospinal fluid;
measuring the level of sepiapterin in the blood and/or plasma;
calculating the ratio of sepiapterin the cerebrospinal fluid:blood and/or plasma;
wherein a lower ratio indicates a decreased central activity and/or penetrance across the blood brain barrier.

28. The method of paragraph 27, wherein a lower ratio indicates a decreased risk of central nervous system related adverse effects and a higher ratio indicates increased risk of such adverse effects.

29. The method of any of paragraphs 27-28, wherein the measurement step comprises performing a liquid chromatography coupled to mass spectrometry or ELISA measurement.

30. The method of any of paragraphs 27-29, further comprising an initial step of administering a SPR inhibitor to a subject.

31. The method of any of paragraphs 27-30, wherein the level of sepiapterin is the extracellular level of sepiapterin.

32. The method of any of paragraphs 27-31, wherein the level of sepiapterin is the intracellular level of sepiapterin.

33. The method of paragraph 32, wherein the intracellular level of sepiapterin is the level in a cell selected from the group consisting of:
a neuron; a white blood cell; a red blood cell; a fibroblast; an epithelial cell; a neural progenitor cell; an embryonic stem cell; and an iPSC.

34. The method of paragraph 33, wherein the cell is a white blood cell.

35. A method of treating a subject with BH4 or BH2, the method comprising:
measuring the level of sepiapterin for monitoring the presence, degree and/or rate of SPR inhibition in a subject; and
administering BH4 and/or BH2 to the subject if the level of sepiapterin is greater than a reference level associated with adverse effects due to excessive SPR inhibition and excessively reduced BH4 and BH2 levels.

36. A method of treating a subject with BH4 or BH2, the method comprising administering BH4 and/or BH2 to a subject determined to have a level of sepiapterin greater than a reference level associated with adverse effects due to excessive SPR inhibition and excessively reduced BH4 and BH2 levels.

37. A method of detecting a loss of function mutation in SPR, the method comprising:
measuring the level of sepiapterin in a sample;
wherein a level of sepiapterin which is increased relative to a reference level indicates the presence of a loss of function mutation of SPR in the sample.

38. A method of detecting a loss of function mutation in SPR, the method comprising:
measuring the level of sepiapterin in a sample in the absence of treatment with an SPRi;
wherein a level of sepiapterin which is increased relative to a reference level indicates the presence of a loss of function mutation of SPR in the sample.

39. The method of any of paragraphs 37-38, wherein an increased level of sepiapterin is a detectable level of sepiapterin.

40. The method of any of paragraphs 37-39, wherein the sample is a sample obtained from a cell culture.

41. The method of any of paragraphs 37-40, wherein the sample is a sample obtained from a subject.

42. The method of any of paragraphs 37-41, wherein the measurement step comprises performing a mass spectroscopy or ELISA measurement.

43. The method of any of paragraphs 37-42, wherein the level of sepiapterin is the extracellular level of sepiapterin.

44. The method of any of paragraphs 37-43, wherein the level of sepiapterin is the intracellular level of sepiapterin.

45. The method of paragraph 44, wherein the intracellular level of sepiapterin is the level in a cell selected from the group consisting of:
a neuron; a white blood cell; a red blood cell; a fibroblast; an epithelial cells; a
neural progenitor cell; an embryonic stem cell; and an iPSC.

46. The method of paragraph 45, wherein the cell is a white blood cell.

47. The method of paragraph 43, wherein the level of extracellular sepiapterin is the level of sepiapterin in a bodily fluid.

48. The method of paragraph 47, wherein the bodily fluid is selected from the group consisting of:
plasma; blood; cerebrospinal fluid; synovial fluid; saliva; tears; and urine.

49. The method of paragraph 48, wherein the bodily fluid is urine.

50. A method of defining the therapeutic index of an SPRi, the method comprising:
administering doses of the sepiapterin reductase inhibitor (SPRi) to a population of subjects;
measuring the level of sepiapterin in the subjects for monitoring the presence, degree and/or rate of SPR inhibition;
defining the $ED_{50}$ as the dose at which 50% of the population a decrease in pain and/or inflammation;
defining the $TD_{50}$ as the dose at which 50% of the population exhibits a level of sepiapterin which is increased relative to a reference level;
and calculating the therapeutic index as the ratio between the $TD_{50}$ and the $ED_{50}$.

51. The method of paragraph 50, wherein the the $TD_{50}$ is defined as the dose at which 50% of the population exhibits a level of sepiapterin which is increased relative to a reference level and at which adverse effects begin to occur from inhibition of SPR.

52. The method of any of paragraphs 50-51, wherein the reference level of sepiapterin is the level in a subject prior to administration of the SPRi.
53. The method of any of paragraphs 50-52, wherein an increased level of sepiapterin is a detectable level of sepiapterin.
54. The method of any of paragraphs 50-53, wherein the level of sepiapterin is the extracellular level of sepiapterin.
55. The method of paragraph 54, wherein the level of extracellular sepiapterin is the level of sepiapterin in a bodily fluid.
56. The method of paragraph 55, wherein the bodily fluid is selected from the group consisting of:
plasma; blood; cerebrospinal fluid; synovial fluid saliva; tears; and urine.
57. The method of paragraph 56, wherein the bodily fluid is urine.
58. The method of any of paragraphs 50-57, wherein the measurement step comprises performing liquid chromatography coupled to mass spectrometry, fluorescent detection, mass spectroscopy, or ELISA measurement.
59. The method of any of paragraphs 50-58, wherein the level of sepiapterin is the intracellular level of sepiapterin.
60. The method of paragraph 59, wherein the intracellular level of sepiapterin is the level in a cell selected from the group consisting of:
a neuron; a white blood cell; a red blood cell; a fibroblast; an epithelial cells; a neural progenitor cell; an embryonic stem cell; and an iPSC.
61. The method of any of paragraphs 60, wherein the cell is a white blood cell.
62. The use of BH4 and/or BH2 for the treatment of a subject, the use comprising
measuring the level of sepiapterin for monitoring the presence, degree and/or rate of SPR inhibition in a subject; and
administering BH4 and/or BH2 to the subject if the level of sepiapterin is greater than a reference level associated with adverse effects due to excessive SPR inhibition and excessively reduced BH4 and BH2 levels.
63. The use of BH4 and/or BH2 for the treatment of a subject, the use comprising administering BH4 and/or BH2 to a subject determined to have a level of sepiapterin greater than a reference level associated with adverse effects due to excessive SPR inhibition and excessively reduced BH4 and BH2 levels.
64. A method of treating a subject with a sepiapterin reductase inhibitor (SPRi), the method comprising:
measuring the level of sepiapterin in a sample obtained from a subject;
administering a therapeutically effective dose of the sepiapterin reductase inhibitor (SPRi) if the level of sepiapterin is at or lower than a reference range; and
not administering a SPRi if the level of sepiapterin is greater than a reference range.
65. The method of paragraph 64, wherein a level of sepiapterin greater than a reference range is a detectable level of sepiapterin.
66. The method of any of paragraphs 64-65, wherein the measurement step comprises performing a mass spectroscopy or ELISA measurement.
67. The method of any of paragraphs 64-66, wherein the level of sepiapterin is the extracellular level of sepiapterin.
68. The method of any of paragraphs 64-66, wherein the level of sepiapterin is the intracellular level of sepiapterin.
69. The method of paragraph 68, wherein the intracellular level of sepiapterin is the level in a cell selected from the group consisting of:
a neuron; a white blood cell; a red blood cell; a fibroblast; an epithelial cells; a neural progenitor cell; an embryonic stem cell; and an iPSC.
70. The method of paragraph 69, wherein the cell is a white blood cell.
71. The method of paragraph 67, wherein the level of extracellular sepiapterin is the level of sepiapterin in a bodily fluid.
72. The method of paragraph 71, wherein the bodily fluid is selected from the group consisting of:
plasma; blood; cerebrospinal fluid; synovial fluid; saliva; tears; and urine.
73. The method of paragraph 71, wherein the bodily fluid is urine.
74. The method of any of paragraphs 64-73, wherein the subject is a subject who has received or is receiving treatment with a sulfa drug.

EXAMPLES

Example 1

Described herein are experiments demonstrating that the pterin, sepiapterin, in plasma and other biological fluids or tissues, can be a biomarker for the inhibition of the activity of the enzyme sepiapterin reductase (SPR) by specific sepiapterin reductase inhibitors (SPRi) Inhibition of SPR results in accumulation of the metabolite sepiapterin and unexpectedly its release from cells into body fluids so that its levels reflect the degree of SPR inhibition and can be a surrogate for reduced BH4 or BH2 levels, while providing advantages over measurement of BH4 and/or BH2 as described elsewhere herein.

Activity of SPRi can be followed by measurement of sepiapterin levels using HPLC-MS/MS (high performance liquid chromatography coupled to tandem mass spectrometry) or other appropriate analytical techniques, e.g., LC-MS/MS (liquid chromatography coupled to tandem mass spectrometry), LC coupled to fluorescent detection. When the enzyme activity is inhibited by SPRi's, the tetrahydrobiopterin (BH4) synthetic pathway is blocked, and the metabolic intermediate sepiapterin accumulates, which is followed by an extracellular secretion of the metabolite. The increased levels of sepiapterin can be measured in tissues, e.g. liver and nervous tissue, cultured cells, and fluids e.g. plasma, urine and cerebrospinal fluid. The increased levels of sepiapterin directly demonstrate inhibition of sepiapterin reductase activity. Measuring levels of sepiapterin following administration of SPRi's can be used to titrate the degree of inhibition of SPR, in vitro and in vivo for drug discovery and for monitoring therapeutic ratio in patients.

Figure 1:
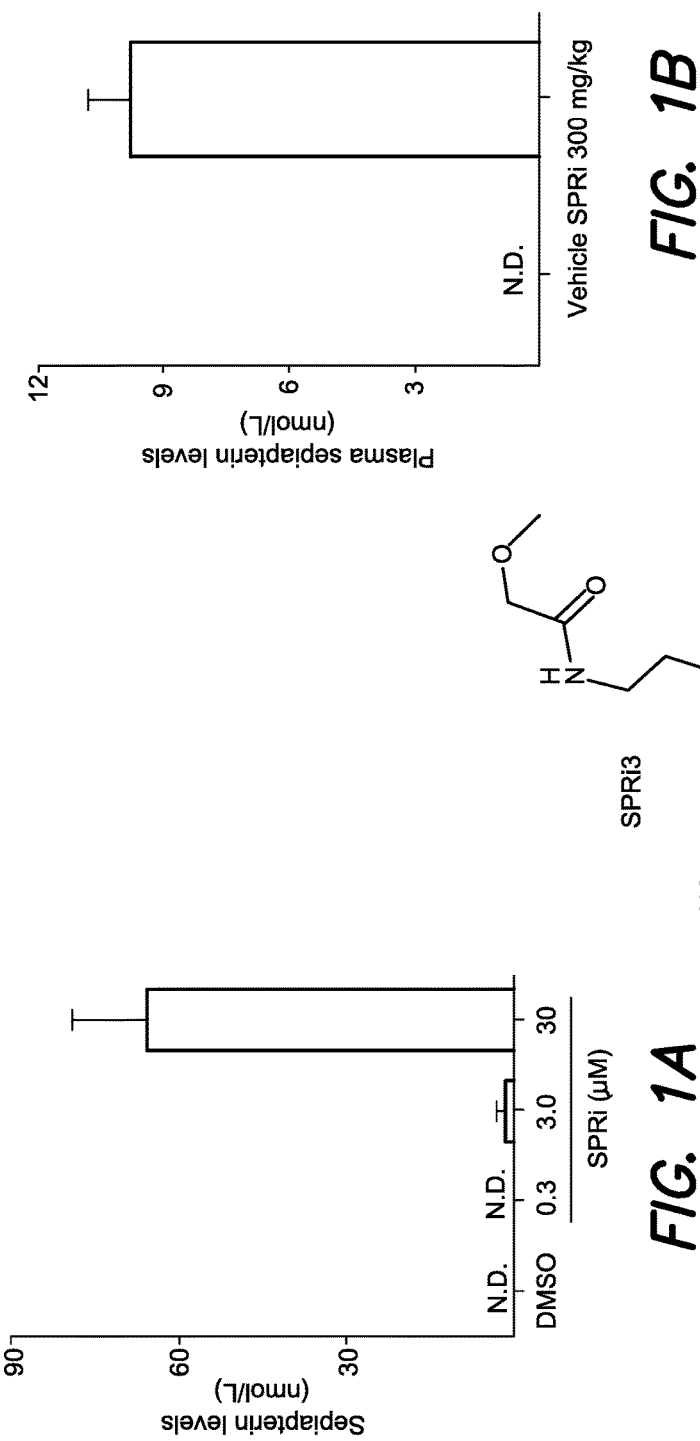
FIGS. 1A-1C demonstrate the effect of an SPR inhibitor (SPRi) on sepiapterin levels in fluids, in vivo and in vitro.
Figure 2:
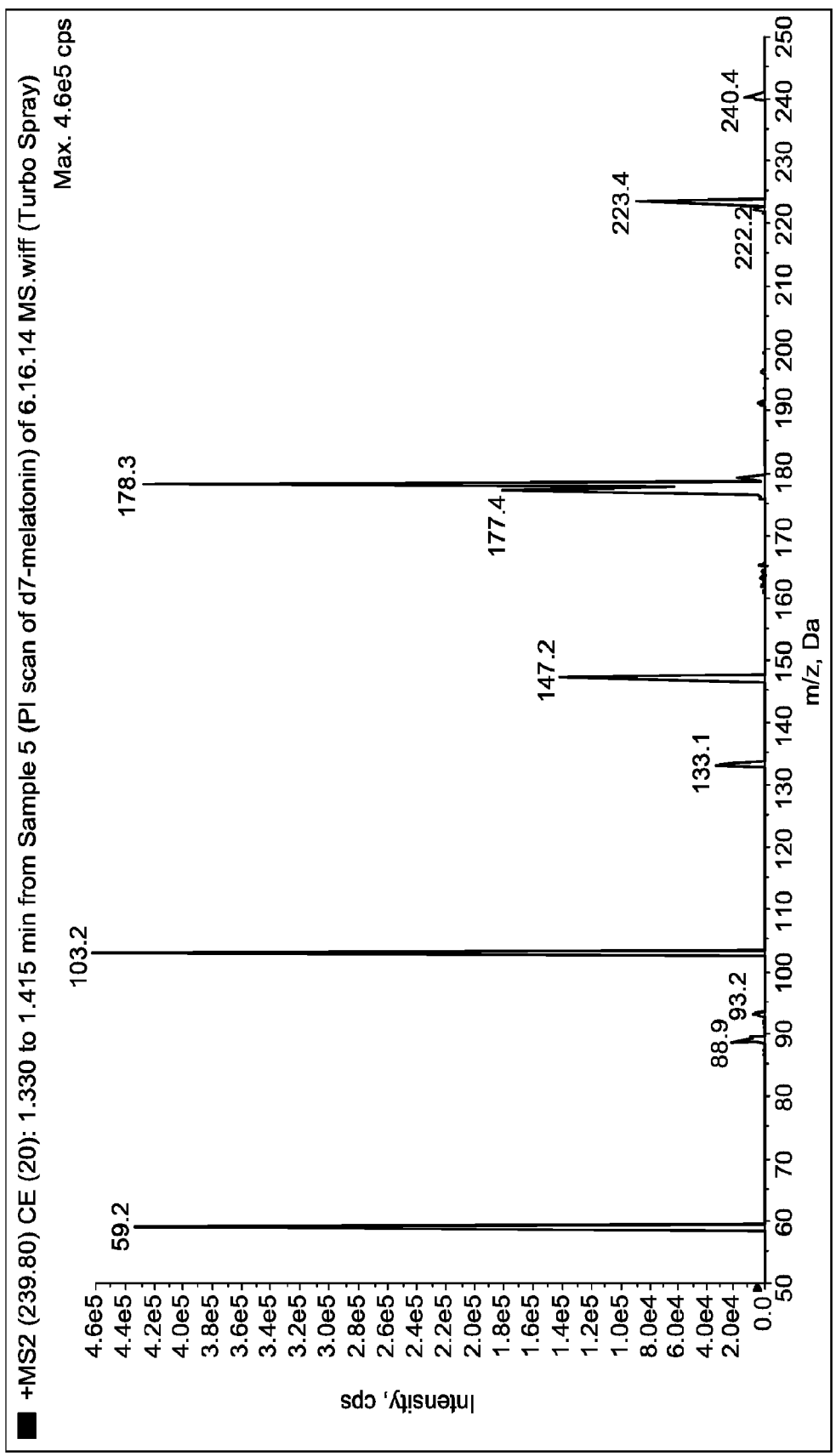
FIG. 2 depicts product ions scan of the internal standard, melatonin-D7.
Figure 3:
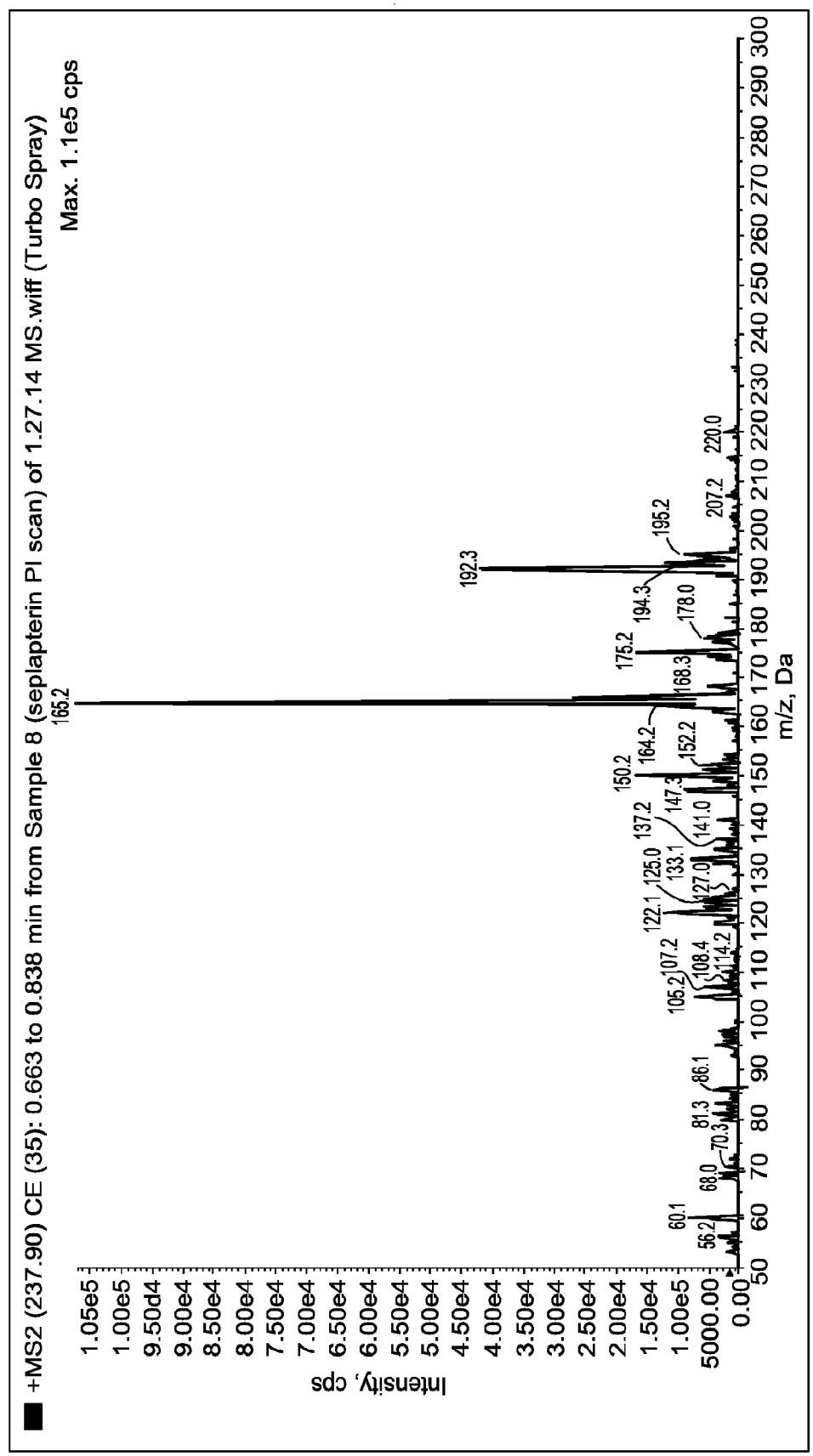
FIG. 3 depicts product ions scan of sepiapterin.
Figure 4A:
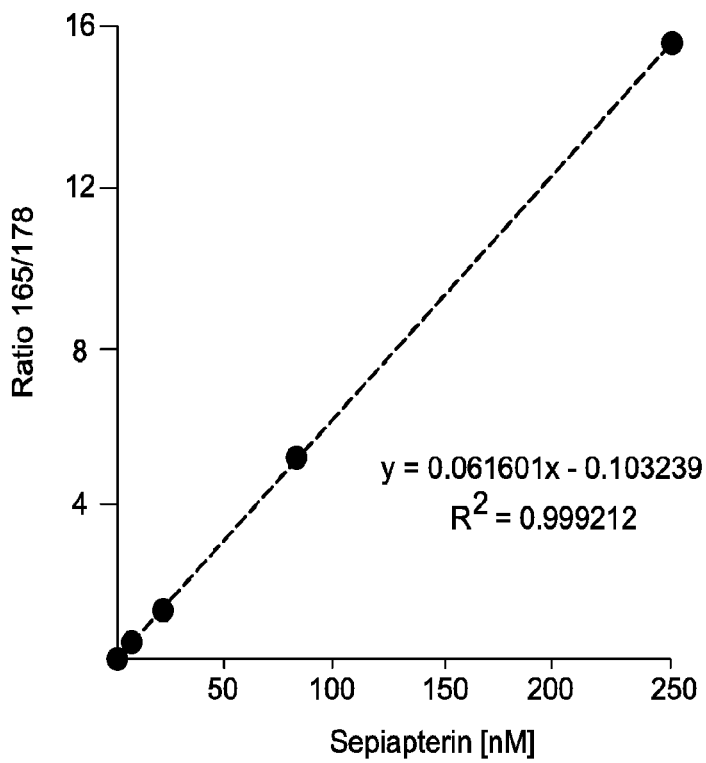
FIGS. 4A-4B depict calibration curves of ion intensity ratio of sepiapterin (165) vs. melatonin-D7 (178; internal standard). Curves show linearity within the range 0.35-250 nM (FIG. 4A) and also within 0.35 to 27.8 nM (FIG. 4B), the anticipated concentration range of sepiapterin in biological samples after mutation or inhibition of SPR.
Figure 4B:
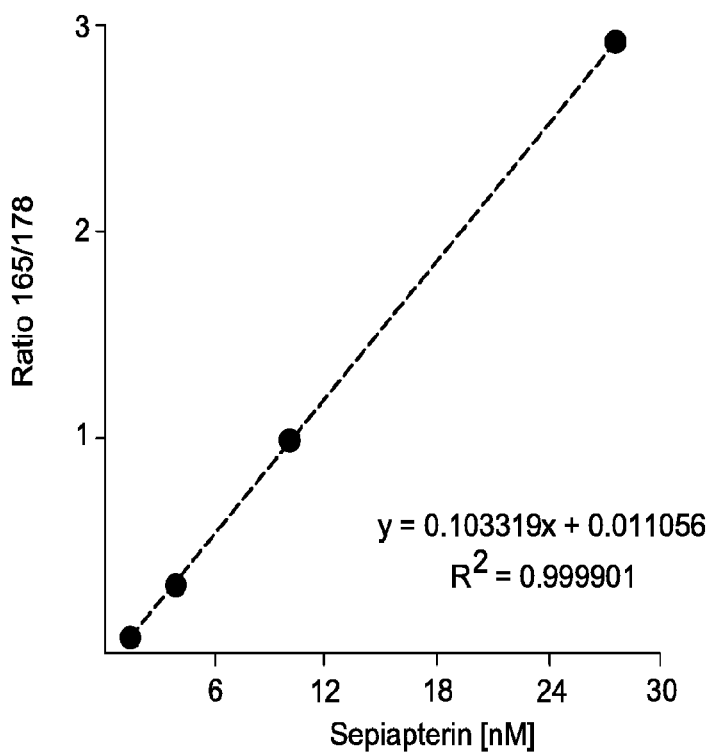

As demonstrated by FIGS. 1A-1B, increased levels of sepiapterin in the supernatant of cultured dorsal root ganglion neurons and in mouse plasma demonstrate SPR inhibition.

Example 2

Determination of Sepiapterin by Liquid Chromatography Coupled to Tandem Mass Spectrometry (LC-MS/MS) in Tissues and Biological Fluids General sample preparation. Tissues, plasma, homogenates from dorsal root ganglia neurons, or cell supernatants are prepared for analysis by adding one volume of 5% trichloroacetic acid (TCA) containing 6.5 mM dithioerythritol. After homogenization, samples are centrifuged at 10,000×g for 10 min at 4° C.

Equipment. AB Sciex QTRAP5500™ mass spectrometer equipped with a Shimadzu HPLC consisting of 2× LC-20AD XR™ pumps and a SIL-20AC XR™ autosampler. The LC column (Agela Technologies, reverse phase C:18; 2.1×50 mm, 2.5μ) is run at room temperature and the autosampler maintained at 4° C. Table 1 lists the LC-MS/MS settings and conditions.

TABLE 1

LC-MS/MS settings and conditions

Mass spectrometer settings

| | |
|---|---|
| Curtain gas | 40 |
| Ion spray voltage | 4500 v |
| Dissolvation temperature | 500° C. |
| GS1 and GS2 | 40 |
| Declustering potential | 10 v |
| Collision energy (CE) for different multiple-reaction-monitoring transitions | |
| Sepiapterin | 237.9/165.2 (CE 34 ev) |
| | 237.9/192.2 (CE 24 ev) |
| Melatonin-D7 | 239.8/178.3 (CE 25 ev) |

Chromatographic conditions: Table 2 lists the chromatography gradient conditions for sepiapterin elution. Information is collected by the MS/MS between 2 & 4.2 min.

| Chromatography gradient conditions | | | |
|---|---|---|---|
| Time (min) | Flow rate (mL/min) | Solvent A (%)[a] | Solvent B (%)[a] |
| 0 | 0.3 | 90 | 10 |
| 3.5 | 0.3 | 5 | 95 |
| 6.5 | 0.3 | 5 | 95 |
| 8.5 | 0.3 | 100 | 0 |
| 11.5 | 0.3 | 100 | 0 |

[a]Solvent A: LC-MS/MS water; solvent B: LC-MS/MS methanol.

Calibrators: Concentrations in the samples are evaluated with a calibration curve, treated in the same way as the samples (0.5 nM to 250 nM). Appropriate blanks and calibrators are analysed between each set of ten samples. LC-MS/NIS peak areas are integrated using Analyst™ 4.0 software. Different flow rates and temperatures in ion source are tested to see the changes in daughter ion intensity ratio.

Figure 5A:
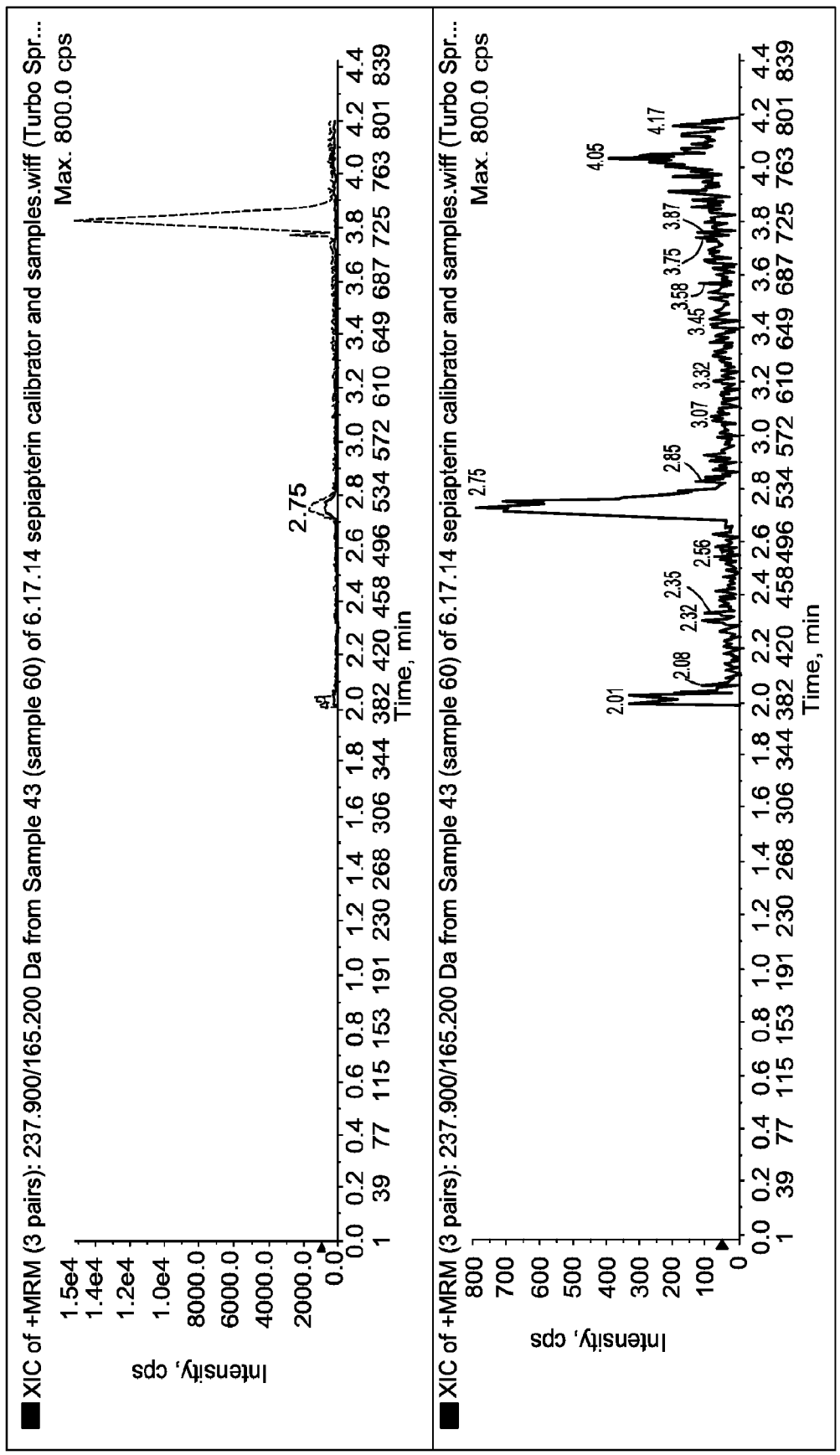
FIGS. 5A-5B depict representative chromatograms for the quantification of sepiapterin levels in supernatants from dorsal root ganglia neurons exposed to one specific inhibitor of sepiapterin reductase activity (SPRi) for 24 h (FIG. 5A). Controls were exposed to medium not containing the SPRi (FIG. 5B). Sepiapterin elutes at 2.75 min and melatonin-D7 (internal standard) at 3.82 min., measured by liquid chromatography coupled to mass spectrometry. Sepiapterin is detected only in samples treated with the SPRi.
Figure 5B:
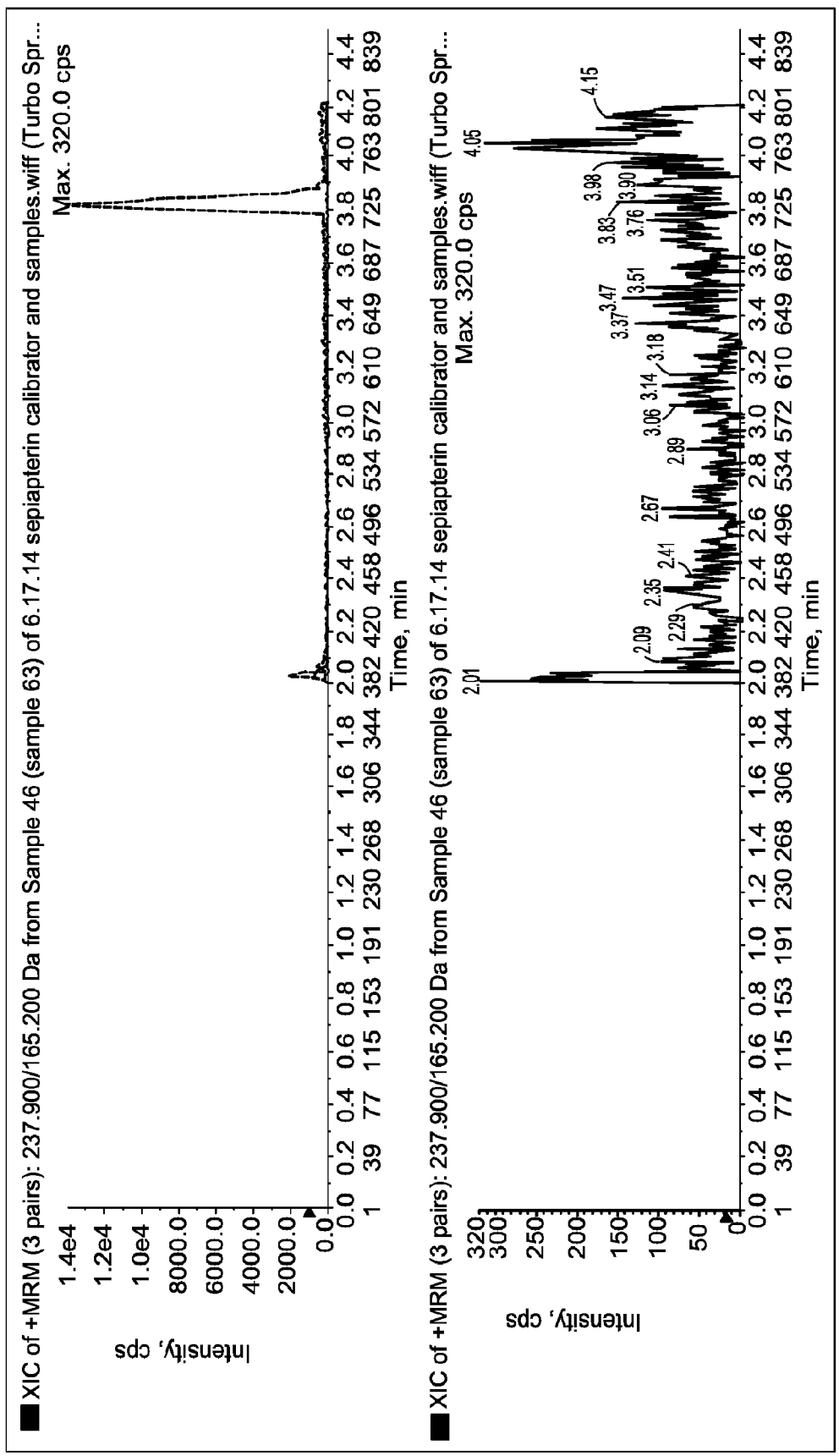
Figure 6A:
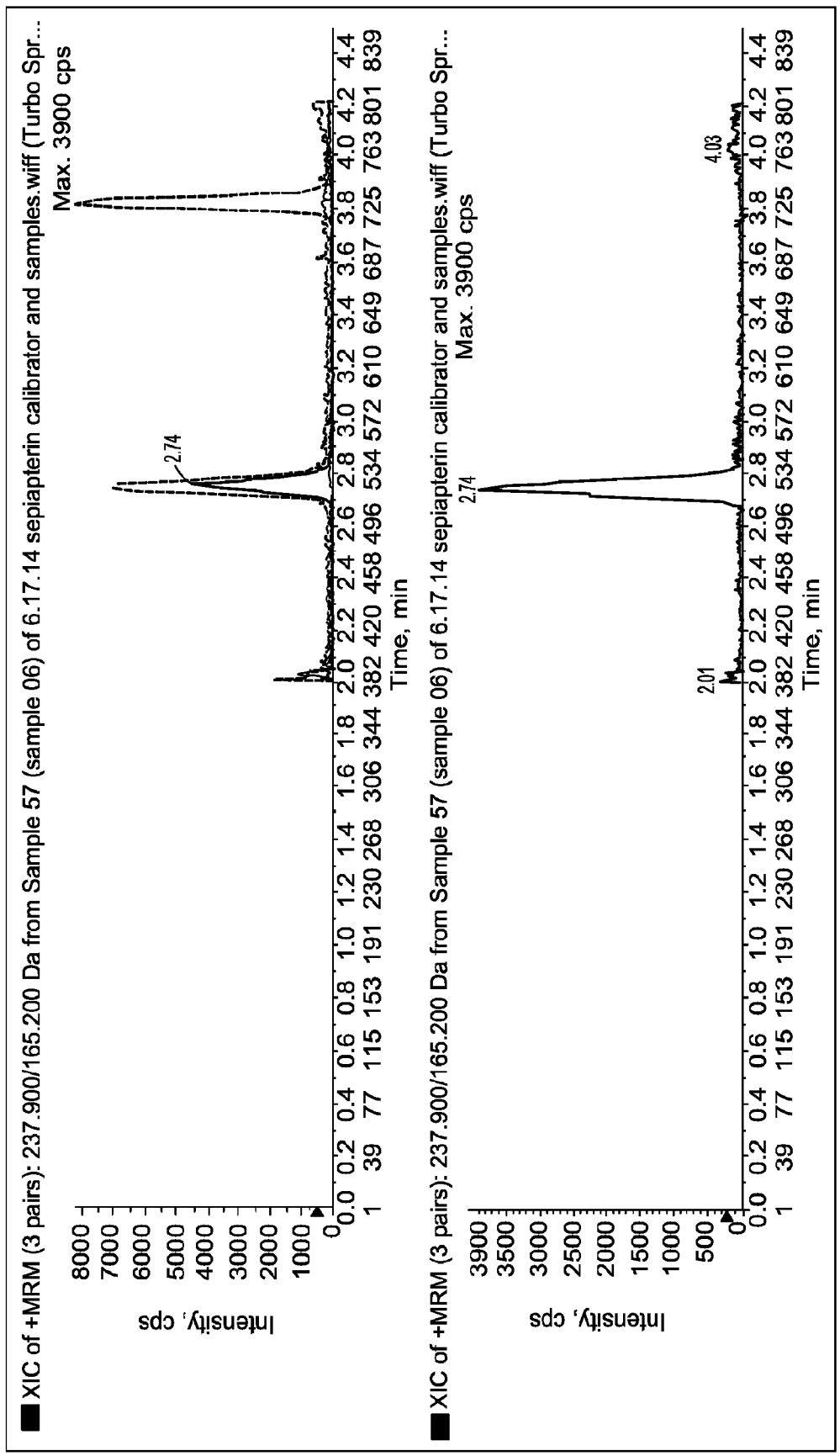
FIGS. 6A-6B depict representative chromatograms for the quantification of sepiapterin levels in plasma from mice treated with (FIG. 6A) one specific inhibitor of sepiapterin reductase activity (SPRi) for five consecutive days (300 mg/kg, i.p.; b.i.d.), 28 days following sciatic nerve injury or (FIG. 6B) vehicle. Sepiapterin elutes at 2.74 min and melatonin-D7 (internal standard) at 3.82 min., measured by liquid chromatography coupled to mass spectrometry. Sepiapterin is detected only in samples from mice treated with the SPRi.
Figure 6B:
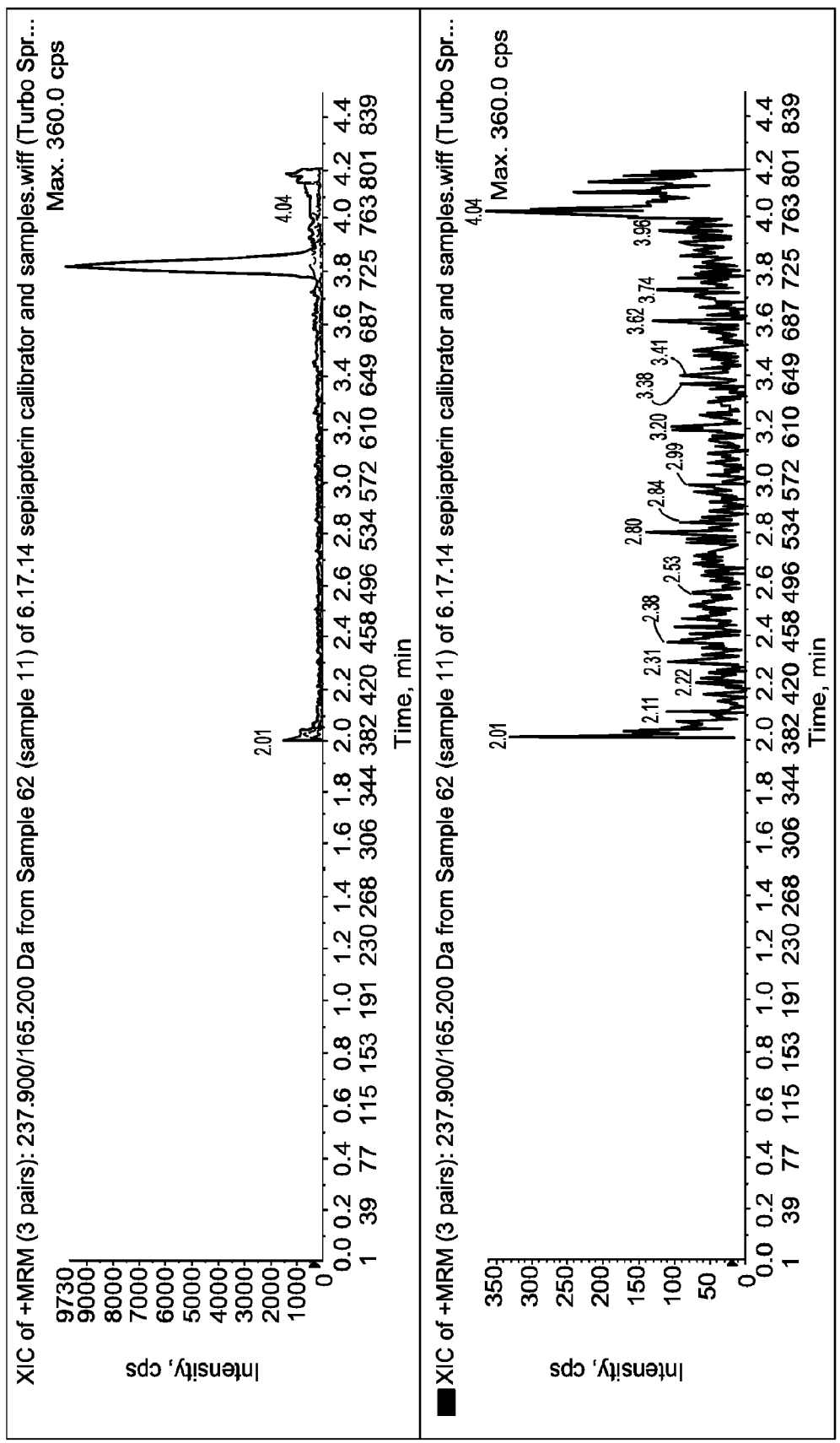

FIGS. 2, 3, and 4A-4B depict representative product ion scans of sepiapterin and the internal standard (melatonin-D7) and the calibration curve (ratio sepiapterin/melatonin-D7). FIGS. 5A-5B and 6 depict chromatograms demonstrating the accumulation of sepiapterin under the effect of one specific inhibitor of sepiapterin reductase activity in different experimental conditions.

Example 3

Figure 7A:
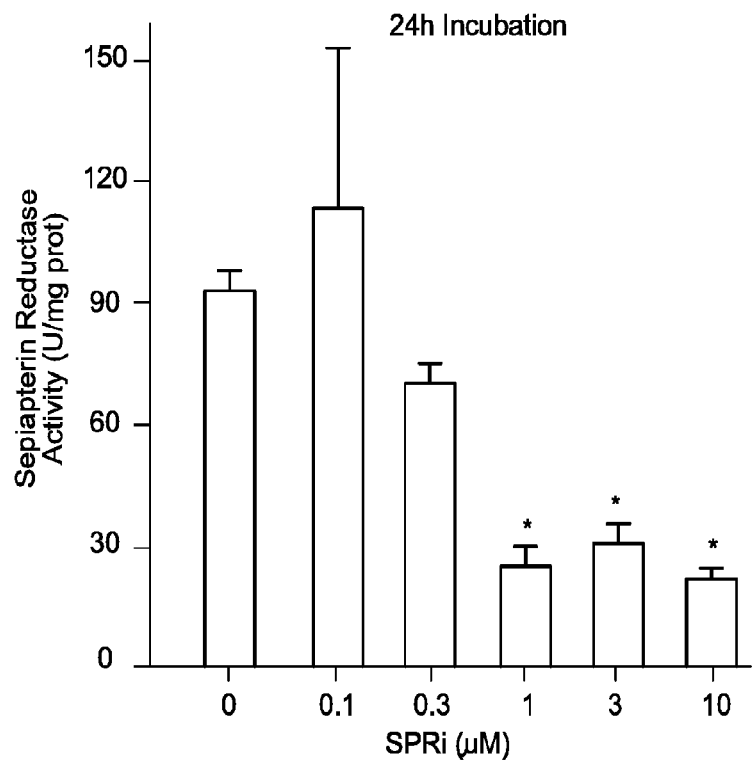
FIG. 7A depicts sepiapterin reductase activity measured by spectrophotometry in primary sensory neurons cultures after 24 hrs incubation with various doses of an SPR inhibitor (n=3-5 samples per condition), (1 unit (U)=μmol consumed sepiapterin/min).
Figure 7B:
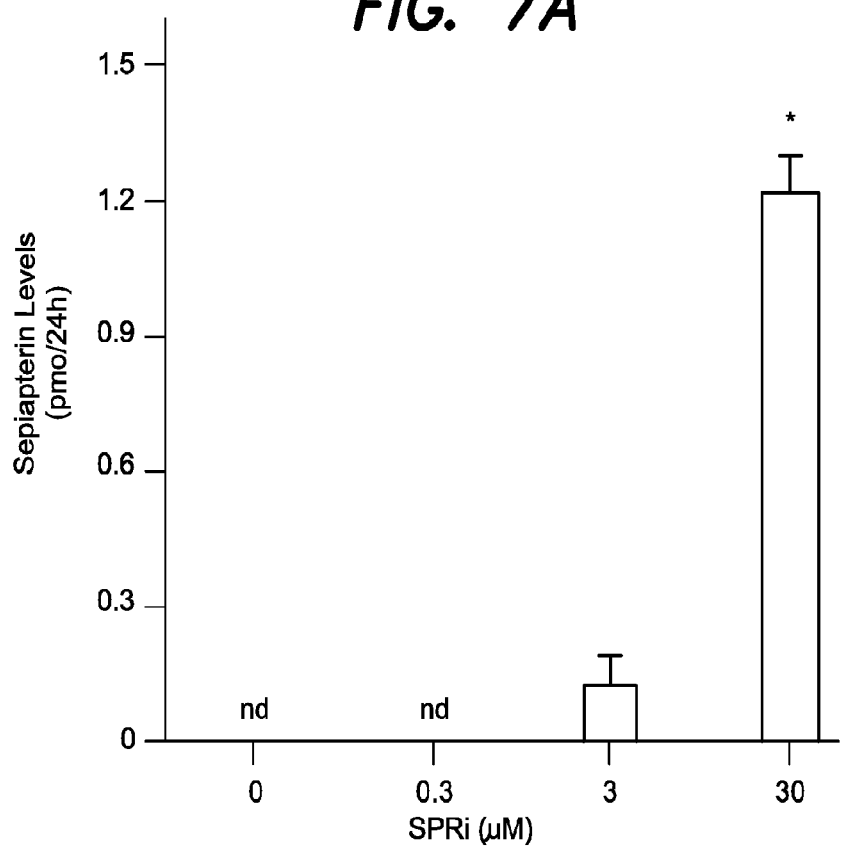
FIG. 7B depicts sepiapterin release after inhibition of SPR activity in mouse dorsal root ganglion neurons (n=3 samples per condition). Results are mean +/−SEM from 3 independent experiments. *: p<0.05 one way ANOVA followed by Tukey post hoc test.

Administration of an SPRi significantly reduced SPR activity in primary cultures of sensory neurons (FIG. 7A) (IC50=0.45 μM) and this was associated with a concomitant accumulation of sepiapterin (FIG. 7B).

Concentrations of sepiapterin in DRG neuron supernatants were determined by liquid chromatography coupled to electrospray ionization tandem mass spectrometry. The method was adapted from Tegeder et al. (2006) and the following optimized multiple-reaction-monitoring (MRM) parameters 237.9>177.2 and 237.9>178.2 were used for sepiapterin identification and quantification Example 4

Sepiapterin levels were measured in the urine of mice administered SPRi3 (300 mg/kg/day) and humans administered a standard clinical dose of sulfasalzine an FDA approved SPRi (2 g/day) (FIG. 9). Prior to administration of the sepiapterin reductase inhibitor, sepiapterin was undetectable in all subjects. FIG. 9 depicts the measurement of sepiapterin in urine. Sepiapterin levels were reduced following washout of SPRi3 in mice (FIG. 9; upper panel).

What is claimed herein is:

1. A method of treating pain or inflammation in a subject in need thereof, the method comprising:
   administering a dose of a sepiapterin reductase inhibitor (SPRi);
   measuring, by mass spectroscopy, fluorescent detection, or ELISA, the level of sepiapterin in a sample obtained from the subject;
   administering an additional dose of the SPRi if the level of sepiapterin is undetectable; and
   administering a decreased dose of the SPRi if the level of sepiapterin is detectable.

2. The assay of claim 1, wherein the level of sepiapterin is the extracellular level of sepiapterin.

3. The method of claim 2, wherein the level of extracellular sepiapterin is the level of sepiapterin in a bodily fluid.

4. The method of claim 3, wherein the bodily fluid is selected from the group consisting of: plasma; blood; cerebrospinal fluid; synovial fluid; saliva; tears; and urine.

5. The assay of claim 3, wherein the bodily fluid is urine.

6. The method of claim 1, wherein the level of sepiapterin is the intracellular level of sepiapterin.

7. The method of claim 6, wherein the intracellular level of sepiapterin is the level in a cell selected from the group consisting of:
   a neuron; a white blood cell; a red blood cell; a fibroblast; an epithelial cell; a neural progenitor cell; an embryonic stem cell; and an iPSC.

8. The method of claim 6, wherein the cell is a white blood cell.

9. The method of claim 1, wherein the SPRi is sulfapyridine, N-(2-(5-hydroxy-2-methyl-1H-indol-3-yflethyl)-2-methoxyacetamide (ACS8099/SPRi3), N-Acetylserotonin, or sulfasalazine.

* * * * *

UNITED STATES PATENT AND TRADEMARK OFFICE
CERTIFICATE OF CORRECTION

PATENT NO. : 10,365,267 B2
APPLICATION NO. : 15/516956
DATED : July 30, 2019
INVENTOR(S) : Clifford J. Woolf et al.

It is certified that error appears in the above-identified patent and that said Letters Patent is hereby corrected as shown below:

In the Claims

At Column 29, Claim 2, Line 28, please replace "assay" with -- method --.

At Column 30, Claim 5, Line 18, please replace "assay" with -- method --.

At Column 30, Claim 9, Lines 30-31, the formula "N-(2-(5-hydroxy-2-methyl-1H-indol-3-yflethyl)-2-methoxyacetamide" should be replaced with -- N-(2-(5-hydroxy-2-methyl-1H-indol-3-yl)ethyl)-2-methoxyacetamide --.

Signed and Sealed this
First Day of October, 2019

Andrei Iancu
*Director of the United States Patent and Trademark Office*

SEQUENCE LISTING

<160> NUMBER OF SEQ ID NOS: 2

<210> SEQ ID NO 1
<211> LENGTH: 1466
<212> TYPE: DNA
<213> ORGANISM: Homo sapiens

<400> SEQUENCE: 1

```
cgcctcctgc ctggtctcgg gtgccagcgc cgccggcgga gaacaggagc atggagggcg      60
ggctggggcg tgctgtgtgc ttgctgaccg gggcctcccg cggcttcggc cggacgctgg     120
ccccgctcct ggcctcgctg ctgtcgcccg gctccgtgct tgtccttagc gcccgcaacg     180
acgaggcact gcgccagctg gaggccgagc tgggcgccga gcggtctggc ctgcgcgtgg     240
tgcgggtgcc cgccgacctg ggcgccgagg ccggcttgca gcagctgctc ggcgccctgc     300
gcgagctccc ccggcccaag gggctgcagc gactgctgct tatcaacaac gcgggctctc     360
ttggggatgt gtccaaaggc ttcgtggacc tgagtgactc cactcaagtg aacaactact     420
gggcactgaa cttgacctcc atgctctgcc tgacttccag cgtcctgaag gccttcccgg     480
```

```
acagtcctgg cctcaacaga accgtggtta acatctcgtc cctctgtgcc ctgcaacctt      540
tcaaaggctg ggcgctgtac tgtgcaggaa aggctgctcg tgatatgctg ttccaggtcc      600
tggcgctgga ggaacctaat gtgagggtgc tgaactatgc cccaggtcct ctggacacag      660
acatgcagca gttggcccgg agacctccg tggacccaga catgcgaaaa gggctgcagg       720
agctgaaggc aaagggggaag ctggtggatt gcaaggtgtc agcccagaaa ctgctgagct     780
tactggaaaa ggacgagttc aagtctggag cccacgtgga cttctatgac aaataagccc     840 atgttttttgg cttcctgaac cttttttgccc ccacttttag acataccccca gagccctgtg   900 gctccccaca ccctgccata ggggcagtcc tgccttacac atagaagcat tcatgcctgc     960
tgccctgccc tcaggcacag ccagctgtga gctcccaggt cattggcctt accagttgtc    1020
aggagtctgt gctgtgcacc ctgggttata aggaggctta ggagagaggt tatgggtatt    1080
ggtgtctcta tccccaggaa tagaacttaa ggggtgggaa gaacaggaaa agaagctgga    1140
acacagaaga gaggaggttg tgtctcttgc tcatagcaag cctgtgggta gaggaaagag    1200
tgatctggtg tcgaatagga ggacccatgt agattcgcag atggcctgga tgggaggaag    1260
ggcagacggt acatgtccca gcccacatag atgcccttg ctgagggtag caggaccttc     1320
tgttgaactt tgtgtcctca ctctgatgtc tccttccttc agaatctacc acccctcccc    1380
caggctggga aaggggctc ctgggtgtct gtatacacgc caaaggcaga tacaaataaa     1440
atacagattg tccttctta aaaaaa                                            1466

<210> SEQ ID NO 2
<211> LENGTH: 261
<212> TYPE: PRT
<213> ORGANISM: Homo sapiens

<400> SEQUENCE: 2

Met Glu Gly Gly Leu Gly Arg Ala Val Cys Leu Leu Thr Gly Ala Ser
1               5                   10                  15

Arg Gly Phe Gly Arg Thr Leu Ala Pro Leu Leu Ala Ser Leu Leu Ser
            20                  25                  30

Pro Gly Ser Val Leu Val Leu Ser Ala Arg Asn Asp Glu Ala Leu Arg
        35                  40                  45

Gln Leu Glu Ala Glu Leu Gly Ala Glu Arg Ser Gly Leu Arg Val Val
    50                  55                  60

Arg Val Pro Ala Asp Leu Gly Ala Glu Ala Gly Leu Gln Gln Leu Leu
65                  70                  75                  80

Gly Ala Leu Arg Glu Leu Pro Arg Pro Lys Gly Leu Gln Arg Leu Leu
                85                  90                  95

Leu Ile Asn Asn Ala Gly Ser Leu Gly Asp Val Ser Lys Gly Phe Val
            100                 105                 110

Asp Leu Ser Asp Ser Thr Gln Val Asn Asn Tyr Trp Ala Leu Asn Leu
        115                 120                 125

Thr Ser Met Leu Cys Leu Thr Ser Ser Val Leu Lys Ala Phe Pro Asp
    130                 135                 140

Ser Pro Gly Leu Asn Arg Thr Val Val Asn Ile Ser Ser Leu Cys Ala
145                 150                 155                 160

Leu Gln Pro Phe Lys Gly Trp Ala Leu Tyr Cys Ala Gly Lys Ala Ala
                165                 170                 175

Arg Asp Met Leu Phe Gln Val Leu Ala Leu Glu Glu Pro Asn Val Arg
            180                 185                 190

Val Leu Asn Tyr Ala Pro Gly Pro Leu Asp Thr Asp Met Gln Gln Leu
```

-continued

```
            195                 200                 205
Ala Arg Glu Thr Ser Val Asp Pro Asp Met Arg Lys Gly Leu Gln Glu
    210                 215                 220

Leu Lys Ala Lys Gly Lys Leu Val Asp Cys Lys Val Ser Ala Gln Lys
225                 230                 235                 240

Leu Leu Ser Leu Leu Glu Lys Asp Glu Phe Lys Ser Gly Ala His Val
                245                 250                 255

Asp Phe Tyr Asp Lys
            260
```